US010617354B2

(12) United States Patent
Berg et al.

(10) Patent No.: US 10,617,354 B2
(45) Date of Patent: Apr. 14, 2020

(54) BIOMETRIC ELECTRODE SYSTEM AND METHOD OF MANUFACTURE

(71) Applicant: MAD Apparel, Inc., Redwood City, CA (US)

(72) Inventors: James Artel Berg, Redwood City, CA (US); Chris Glaister, Redwood City, CA (US); Dhananja Pradhan Jayalath, Redwood City, CA (US); Hamid Hameed Butt, Redwood City, CA (US); Gaston MacMillan, Redwood City, CA (US); Christopher John Wiebe, Redwood City, CA (US)

(73) Assignee: MAD Apparel, Inc., Redwood City, CA (US)

( * ) Notice: Subject to any disclaimer, the term of this patent is extended or adjusted under 35 U.S.C. 154(b) by 723 days.

(21) Appl. No.: 14/699,730

(22) Filed: Apr. 29, 2015

(65) Prior Publication Data

US 2015/0305677 A1 Oct. 29, 2015

Related U.S. Application Data

(60) Provisional application No. 61/985,874, filed on Apr. 29, 2014, provisional application No. 62/044,683, filed on Sep. 2, 2014.

(51) Int. Cl.
*A61B 5/04* (2006.01)
*A61B 5/00* (2006.01)

(52) U.S. Cl.
CPC .............. *A61B 5/6804* (2013.01); *A61B 5/04* (2013.01); *A61B 5/7207* (2013.01); *A61B 2562/125* (2013.01)

(58) Field of Classification Search
CPC ........ A61B 5/6804; A61B 5/04; A61N 1/0484
See application file for complete search history.

(56) References Cited

U.S. PATENT DOCUMENTS

| 3,534,727 A | 10/1970 | Roman |
| 3,973,099 A | 8/1976 | Morris |
| 4,400,341 A | 8/1983 | Sorensen |
| 4,729,377 A | 3/1988 | Granek et al. |
| 6,002,957 A | 12/1999 | Finneran |

(Continued)

FOREIGN PATENT DOCUMENTS

WO 2006119345 A2 11/2006

*Primary Examiner* — Tammie K Marlen
(74) *Attorney, Agent, or Firm* — Fenwick & West LLP

(57) ABSTRACT

An electrode system for sensing biometric signals from a body region of a user and a method of manufacture thereof, the electrode system comprising: a substrate comprising a reference region and a signal communication region, the signal communication region including a set of conductive leads; a set of biosensing contacts coupled to the set of conductive leads; a non-conductive region ensheathing each of the set of biosensing contacts, the non-conductive region including: a set of openings that expose at least a portion of each of the set of biosensing contacts for interfacing with the body region of the user, upon coupling of the electrode system to the user; a first bonding layer that couples the substrate to a fabric base; and a second bonding layer coupled to the first bonding, wherein the substrate is hermetically sealed between the first bonding layer and the second bonding layer.

18 Claims, 16 Drawing Sheets

(56) References Cited

U.S. PATENT DOCUMENTS

| | | |
|---|---|---|
| 6,350,129 B1 | 2/2002 | Gorlick |
| 6,381,482 B1 | 4/2002 | Jayaraman et al. |
| 6,970,731 B1 | 11/2005 | Jayaraman et al. |
| 6,978,684 B2 | 12/2005 | Nurse |
| 7,146,221 B2 * | 12/2006 | Krulevitch ............ A61N 1/0543 607/116 |
| 7,173,437 B2 | 2/2007 | Hervieux et al. |
| 7,474,910 B2 | 1/2009 | Hassonjee et al. |
| 7,559,902 B2 | 7/2009 | Ting et al. |
| 7,602,301 B1 | 10/2009 | Stirling et al. |
| 7,783,334 B2 | 8/2010 | Nam et al. |
| 7,821,407 B2 | 10/2010 | Shears et al. |
| 7,825,815 B2 | 11/2010 | Shears et al. |
| 7,978,081 B2 | 7/2011 | Shears et al. |
| 8,006,633 B2 | 8/2011 | Bennett et al. |
| 8,032,199 B2 | 10/2011 | Linti et al. |
| 8,146,171 B2 | 4/2012 | Chung et al. |
| 8,214,007 B2 | 7/2012 | Baker et al. |
| 8,267,701 B2 | 9/2012 | Beaman et al. |
| 8,280,503 B2 | 10/2012 | Linderman |
| 8,475,371 B2 | 7/2013 | Derchak et al. |
| 8,560,044 B2 | 10/2013 | Kurzweil et al. |
| 8,750,959 B2 | 6/2014 | Lindberg et al. |
| 8,798,708 B2 | 8/2014 | Tremblay |
| 8,818,478 B2 | 8/2014 | Scheffler et al. |
| 8,821,305 B2 | 9/2014 | Cusey et al. |
| 8,909,318 B2 | 12/2014 | Nordstrom |
| 9,119,594 B2 * | 9/2015 | Oleson ................ A61B 5/6804 |
| 2004/0187184 A1 | 9/2004 | Rubin et al. |
| 2004/0254624 A1 | 12/2004 | Johnson |
| 2005/0177059 A1 | 8/2005 | Koivumaa et al. |
| 2006/0246730 A1 | 11/2006 | Stivoric et al. |
| 2007/0038057 A1 | 2/2007 | Nam et al. |
| 2007/0073131 A1 * | 3/2007 | Ryu .................... A41D 13/1281 600/388 |
| 2008/0092341 A1 | 4/2008 | Ahmadshahi |
| 2008/0096726 A1 | 4/2008 | Riley et al. |
| 2009/0012408 A1 | 1/2009 | Nagata et al. |
| 2009/0024017 A1 | 1/2009 | Ruffini et al. |
| 2010/0041974 A1 | 2/2010 | Ting et al. |
| 2010/0117837 A1 | 5/2010 | Stirling et al. |
| 2010/0130847 A1 * | 5/2010 | Dunagan .............. A61B 5/0408 600/389 |
| 2010/0185398 A1 | 7/2010 | Berns et al. |
| 2010/0204616 A1 | 8/2010 | Shears et al. |
| 2010/0234715 A1 | 9/2010 | Shin et al. |
| 2010/0251454 A1 | 10/2010 | Kiernan |
| 2010/0324405 A1 | 12/2010 | Niemi et al. |
| 2011/0257546 A1 | 10/2011 | Gozzini et al. |
| 2011/0288605 A1 | 11/2011 | Kaib et al. |
| 2012/0068759 A1 | 3/2012 | Clark et al. |
| 2012/0165645 A1 | 6/2012 | Russell et al. |
| 2012/0208156 A1 | 8/2012 | Rocklin |
| 2012/0330126 A1 | 12/2012 | Hoppe et al. |
| 2013/0077263 A1 | 3/2013 | Oleson et al. |
| 2013/0137943 A1 | 5/2013 | Rodrigues |
| 2013/0137956 A1 | 5/2013 | Okuda et al. |
| 2013/0172722 A1 | 7/2013 | Ninane et al. |
| 2013/0192071 A1 | 8/2013 | Esposito et al. |
| 2013/0324368 A1 | 12/2013 | Aragones et al. |
| 2013/0338472 A1 * | 12/2013 | Macia Barber .... A61B 5/04085 600/388 |
| 2014/0070949 A1 | 3/2014 | Chen |
| 2014/0097944 A1 | 4/2014 | Fastert et al. |
| 2014/0135593 A1 | 5/2014 | Jayalth et al. |
| 2014/0142459 A1 | 5/2014 | Jayalth et al. |
| 2014/0172134 A1 | 6/2014 | Meschter |
| 2014/0180023 A1 | 6/2014 | Stivoric et al. |
| 2014/0189928 A1 | 7/2014 | Oleson et al. |
| 2014/0275888 A1 | 9/2014 | Wegerich et al. |
| 2014/0296651 A1 | 10/2014 | Stone |
| 2014/0352023 A1 | 12/2014 | Mordecai et al. |
| 2015/0047091 A1 | 2/2015 | Fournier et al. |
| 2015/0148619 A1 | 5/2015 | Berg et al. |
| 2015/0181692 A1 | 6/2015 | Jezewski et al. |

* cited by examiner coupling a volume of conductive polymer to each of the set of conductive leads, thereby forming a set of biosensing contacts coupled to the set of conductive leads of the signal communication region — S220 forming a surface feature comprising a set of protrusions at a surface of at least one of the set of biosensing contacts configured to face skin of the user, wherein the set of protrusions facilitates maintenance of contact between the electrode system and skin of the user — S221

FIGURE 11 for each of the set of biosensing contacts, isolating the volume of conductive polymer with a non-conductive material layer having a set of openings that expose at least a portion of each of the set of biosensing contacts — S230 forming a surface feature comprising a set of protrusions at a surface of the non-conductive material layer configured to face skin of the user, wherein the set of protrusions facilitates maintenance of contact between the electrode system and skin of the user — S231 applying a barrier of a porous material configured at the non-conductive material layer, between each of the set of biosensing contacts, wherein the barrier prevents sweat or other moisture from bridging contacts of the set of biosensing contacts — S232

FIGURE 12

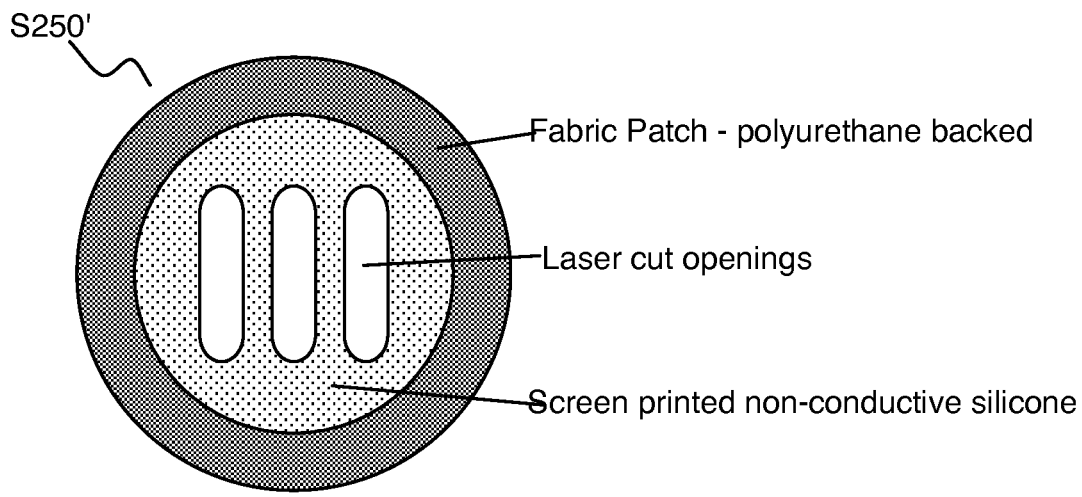
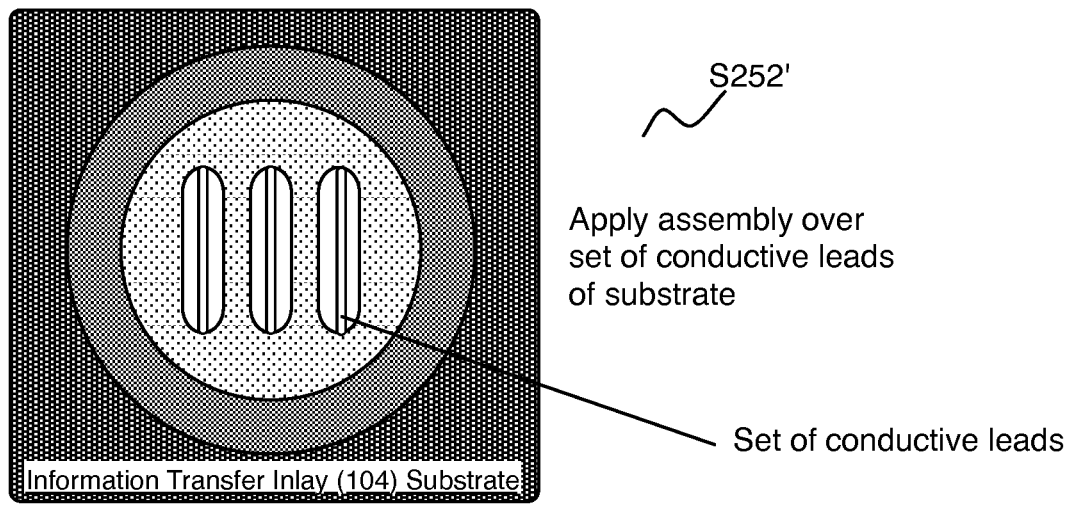
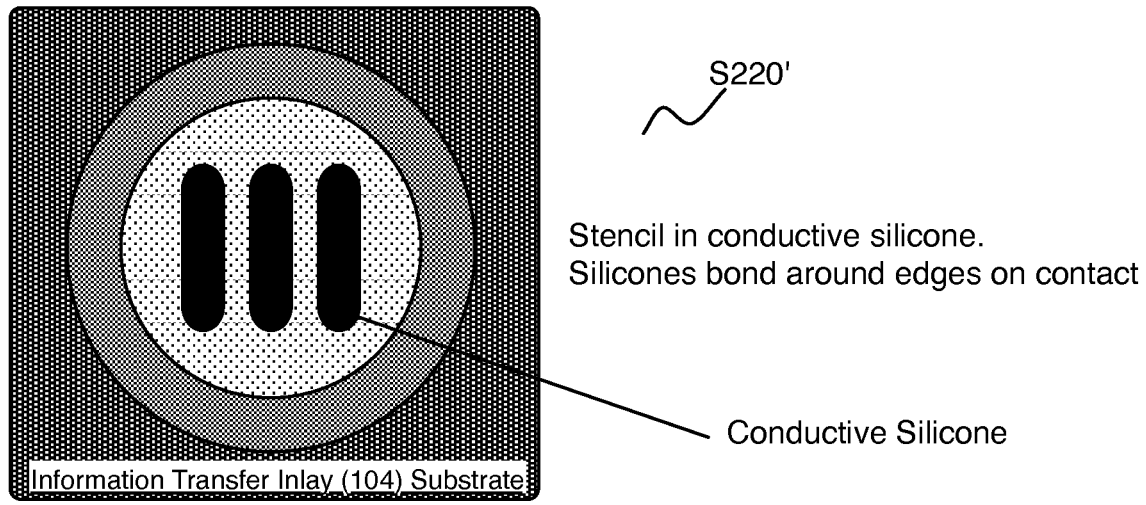
FIGURE 14A

S250'
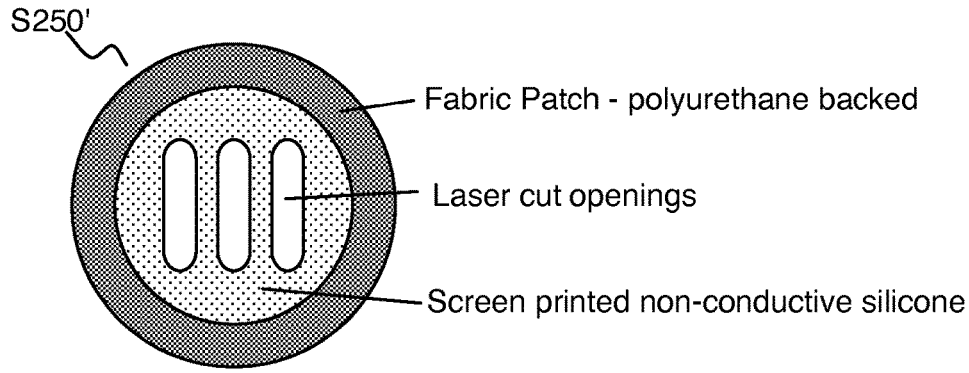
- Fabric Patch - polyurethane backed
- Laser cut openings
- Screen printed non-conductive silicone
1. Abrade non-conductive silicone (e.g., with 120 grit sand paper), then wipe clean with alcohol
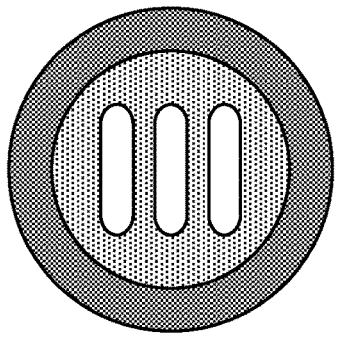
2. Heat press assembly over set of conductive leads
S252'
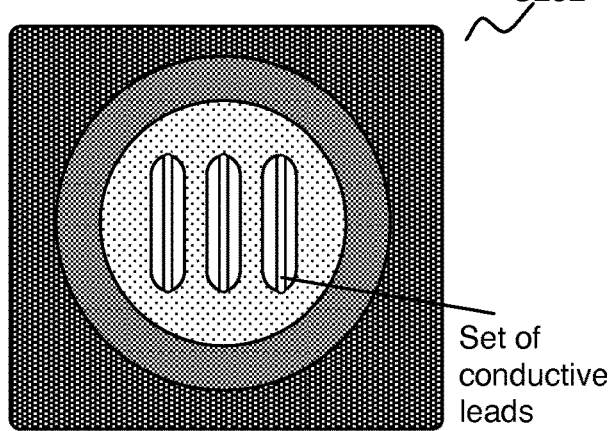
Set of conductive leads
3. Apply primer to assembly edges
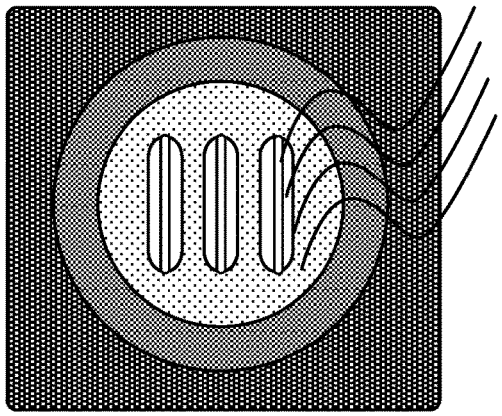
4. Stencil in conductive silicone and press
S220'
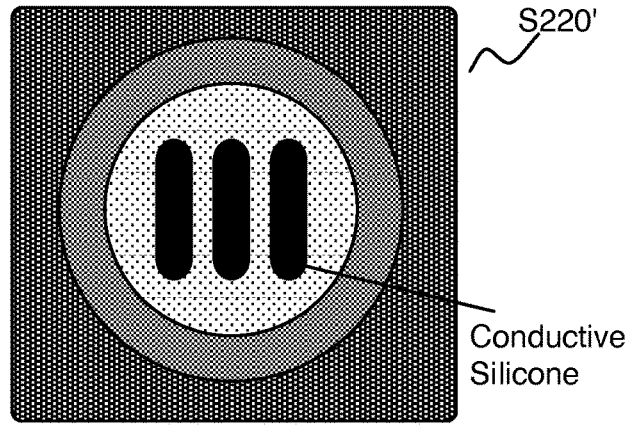
Conductive Silicone
FIGURE 14B S250'
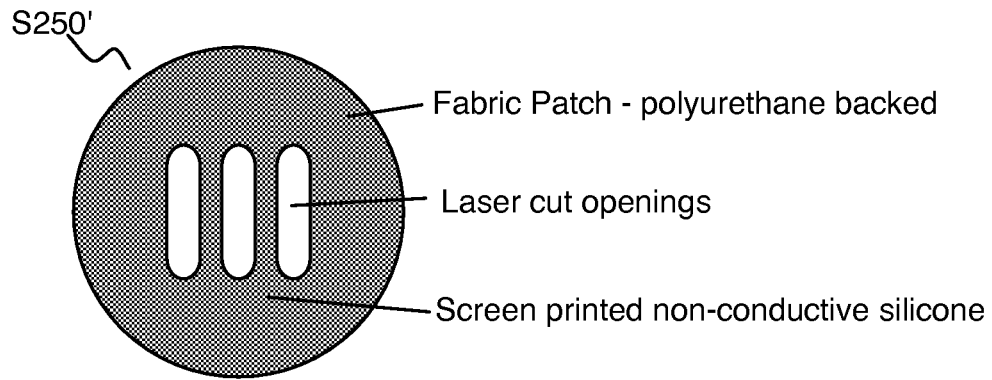
Fabric Patch - polyurethane backed
Laser cut openings
Screen printed non-conductive silicone
1. Heat press assembly over set of conductive leads
S252'
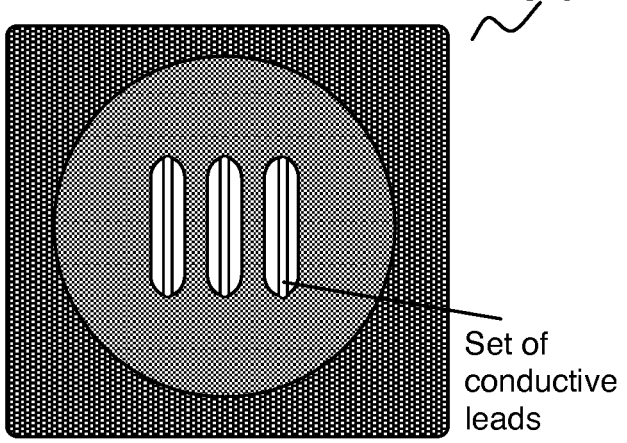
Set of conductive leads
2. Apply primer to assembly edges
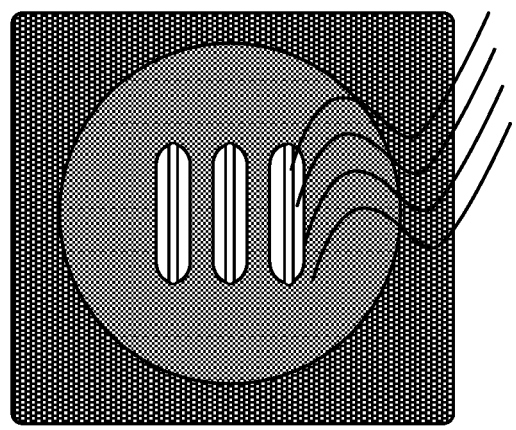
3. Stencil in conductive silicone and press
S220'
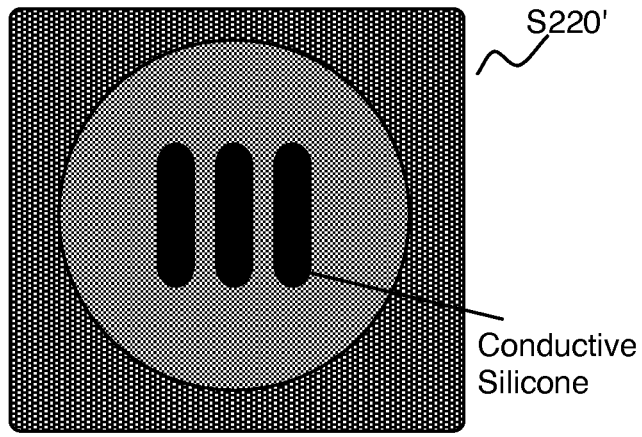
Conductive Silicone
FIGURE 14C

BIOMETRIC ELECTRODE SYSTEM AND METHOD OF MANUFACTURE

CROSS-REFERENCE TO RELATED APPLICATIONS

This application claims the benefit of U.S. Provisional Application Ser. No. 61/985,874 filed 29 Apr. 2014, and U.S. Provisional Application Ser. No. 62/044,683 filed 2 Sep. 2014, which are each incorporated in its entirety herein by this reference.

TECHNICAL FIELD

This invention relates generally to the biometric device field, and more specifically to a new and useful system and method for monitoring biometric signals.

BACKGROUND

Tracking biometric parameters resulting from periods of physical activity can provide profound insights into improving one's performance and overall health. Historically, users have tracked their exercise behavior by manually maintaining records of aspects of their physical activity, including time points, durations, and/or other metrics (e.g., weight lifted, distance traveled, repetitions, sets, etc.) of their exercise behavior. Exercise tracking systems and software have been recently developed to provide some amount of assistance to a user interested in tracking his/her exercise behavior; however, such systems and methods still suffer from a number of drawbacks. In particular, many systems require a significant amount of effort from the user (e.g., systems rely upon user input prior to and/or after a period of physical activity), capture insufficient data (e.g., pedometers that estimate distance traveled, but provide little insight into an amount of physical exertion of the user), provide irrelevant information to a user, and are incapable of detecting body-responses to physical activity at a resolution sufficient to provide the user with a high degree of body awareness. Other limitations of conventional biometric monitoring devices include one or more of: involvement of single-use electrodes, involvement of electrodes that have limited reusability, involvement of a single electrode targeting a single body location, use of adhesives for electrode placement, electrode configurations that result in user discomfort (e.g., strap-based systems), electrode configurations that are unsuited to motion-intensive activities of the user, and other deficiencies.

There is thus a need in the biometric device field to create a new and useful biometric electrode system and method of manufacture. This invention provides such a new and useful system and method.

BRIEF DESCRIPTION OF THE FIGURES

FIGS. 11 and 12 depict variations of a portion of a method for manufacturing an electrode system;

FIGS. 14A-14C depict specific examples of a method for manufacturing an electrode system.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. System

Figure 1A:
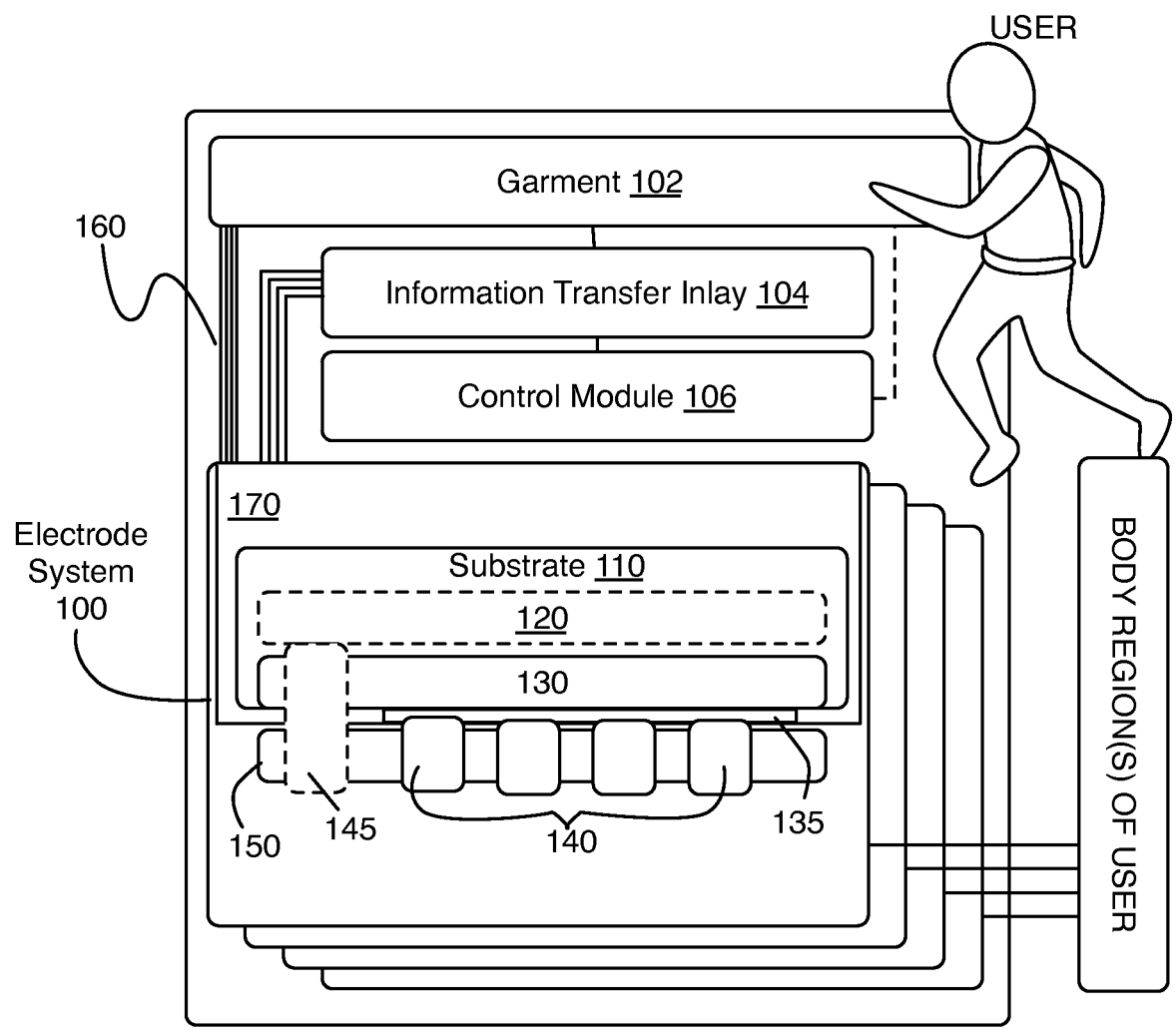
FIGS. 1A and 1B depict embodiments of an electrode system.
Figure 1B:
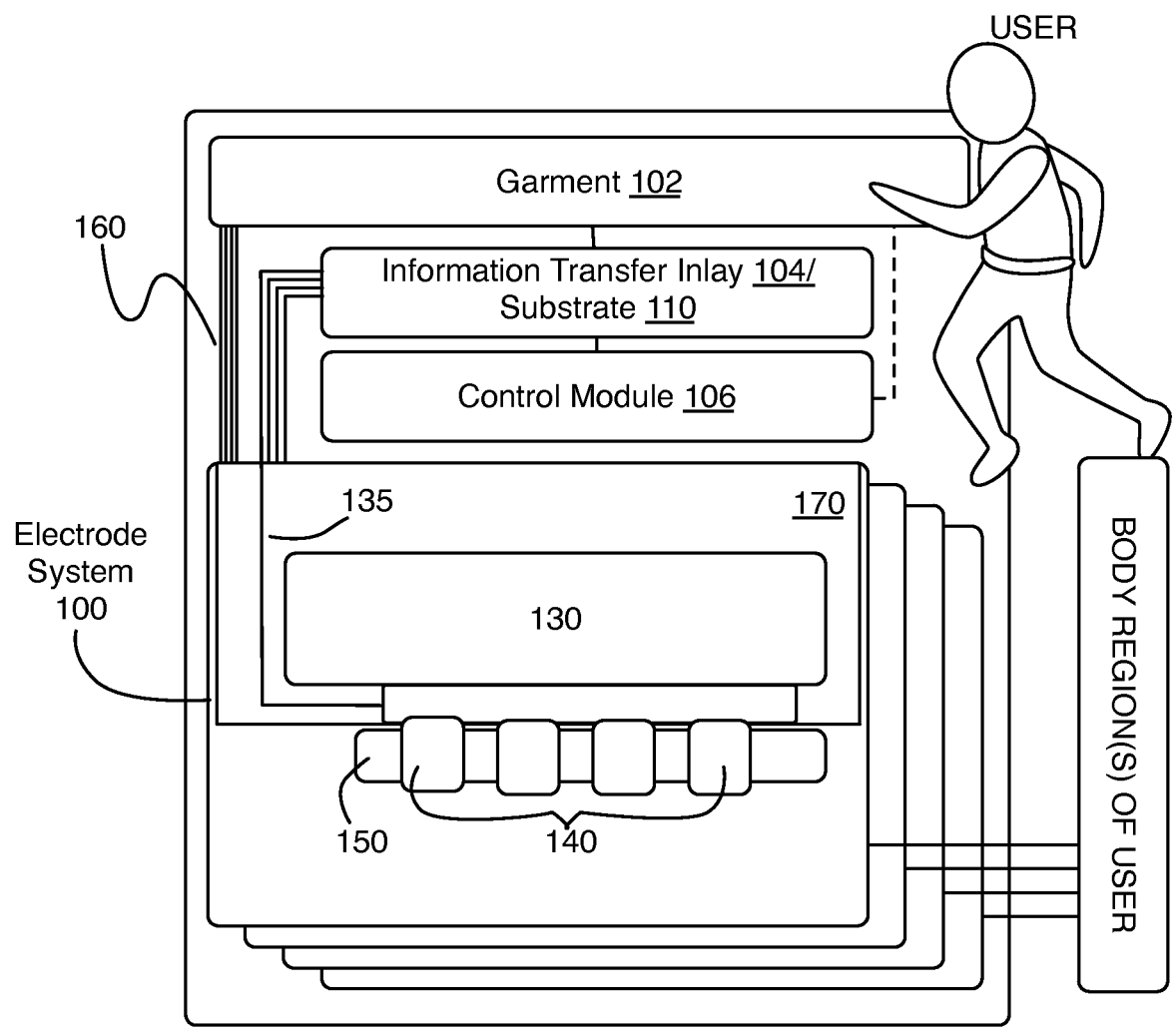

As shown in FIGS. 1A and 1B, an embodiment of a system 100 for sensing biometric signals from a body region of a user comprises: a substrate no comprising a reference conductive region 120 and a signal communication region 130 coupled to the reference conductive region, the signal communication region 130 including a set of conductive leads 135; a set of biosensing contacts 140 coupled to the set of conductive leads 135 of the signal communication region 130; a non-conductive region 150 ensheathing each of the set of biosensing contacts; a first bonding layer 160 that couples the substrate to fabric of a garment; and a second bonding layer 170 coupled to the first bonding layer 160, wherein the substrate 110 is sealed (e.g., sealed from liquid penetration) between the first bonding layer 160 and the second bonding layer 170.

The system 100 functions to detect one or more biometric signals from one or more body regions of a user who is performing a type of physical activity, wherein processing of the detected biometric signals is used to provide information to the user in substantially near real time, such that the user can gain insights into how to maintain or improve performance of the physical activity in a beneficial manner. In variations, the biometric electrode system 100 is configured to detect bioelectrical signals generated at a region of the body of a user who is exercising (e.g., performing aerobic exercise, performing anaerobic exercise), wherein a plurality of units of the system 100 can be positioned at multiple body regions of the user, in order to generate a holistic representation of one or more biometric parameters relevant to activity of the user.

As such, bioelectrical signals detectable, processable, and/or analyzable by the system 100 can include any one or more of: electromyograph (EMG) signals, electrocardiography (ECG) signals, electroencephalograph (EEG) signals, galvanic skin response (GSR), bioelectrical impedance (BIA), and any other suitable bioelectrical signal of the user. The system 100 can, however, be configured to detect, process, and/or analyze any other suitable biosignal data of the user, including one or more of: muscle activity data, heart rate data, movement data, respiration data, location data, environmental data (e.g., temperature data, light data, etc.), and any other suitable data.

Preferably, the electrode system 100 is configured to be integrated with a garment worn by a user during a period of physical activity, as described in U.S. application Ser. No. 14/541,446, entitled "System and Method for Monitoring Biometric Signals" and filed on 14 Nov. 2014, U.S. application Ser. No. 14/079,629, entitled "Wearable Architecture and Methods for Performance Monitoring, Analysis, and Feedback" and filed on 13 Nov. 2013, and U.S. application Ser. No. 14/079,621, entitled "Wearable Performance Monitoring, Analysis, and Feedback Systems and Methods" and filed on 30 Jan. 2014, each of which is incorporated herein in its entirety by this reference. As such, the system 100 is preferably configured to provide a liquid-tight interface (e.g., by way of a seal) in relation to skin of the user, upon coupling of the electrode system 100 to the user, such that sweat or water cannot penetrate the system 100 and interfere with sensitive portions (e.g., conductive leads) of the system 100 during use. Even further, in relation to integration with a garment, the electrode system 100 is preferably configured to be washable (i.e., hand-washable, machine washable, etc.), to omit any requirement for adhesive coupling to a user using hydrogel coupling media, to be low-maintenance without any need for wetting (e.g., with saline), to provide good surface tack in relation to an interface with skin of the user while the user is in motion, and to be shielded from and reduce any interference generated from the body of the user (e.g., interference due to generation of static, interference in the form of common noise, etc.).

The system 100 is preferably configured to be used by a user who is away from a research or clinical setting, such that the user is interfacing with a portion of the system 100 while he or she undergoes periods of physical activity in a natural setting (e.g., at a gym, outdoors, etc.). The system 100 can additionally or alternatively be configured to be operated by a user who is in a research setting, a clinical setting, or any other suitable setting. Embodiments, variations, and/or examples of the system 100 can be manufactured according to embodiments, variations, and/or examples of the method 200 described in Section 2 below; however, the system 100 can additionally or alternatively be fabricated using any other suitable method.

1.1 System—Supporting Elements

As noted above and as shown in FIG. 1, the electrode system 100 can be integrated with a wearable garment 102, including an information transfer inlay 104 configured to facilitate signal transmission from the electrode system 100, and a portable control module 106 configured to couple to the garment by way of a mount in communication with the information transfer inlay, in order to receive signals from the information transfer inlay 104.

The garment 102 is preferably composed of a form-fitting and washable material that is configured to be worn on at least a portion of a user's body. As such, the garment can bias an electrode system 100, coupled to the garment, against skin of the user, when the garment 102 is worn by the user. The garment 102 can thus include a stretchable and/or compressive fabric comprising natural and/or synthetic fibers (e.g., nylon, lycra, polyester, spandex, etc.) to promote coupling (i.e., electrical coupling, mechanical coupling) and/or reduce motion artifacts that could otherwise result from relative motion between the skin of the user and the electrode system 100. In examples, the garment 102 can include any one or more of: a top (e.g., shirt, jacket, tank top, etc.), bottom (e.g., shorts, pants, etc.), elbow pad, knee pad, arm sleeve, leg sleeve, socks, undergarment, neck wrap, glove, and any other suitable wearable garment. Furthermore, the wearable garment 102 can include one or more slots, pouches, ports, bases, pathways, channels, cradles, or other features by which an information transfer inlay 104, portable control module 106, and/or electrode system 100 (described in more detail below) can permanently or removably couple to the wearable garment 102. As such, the garment 102 functions to position one or more units of the electrode system 100 proximal one or more body regions of the user, in order to enable detection of biometric signals from specific body regions of the user as the user is performing a form of physical exercise. In particular, the garment 102 can thus allow elements to be reliably positioned relative to the body of the user, without involving straps or any other coupling elements typically used to retain an electrode in position at a body region of a user. However, alternative variations of the system 100 can be configured to cooperate with straps and/or any other suitable elements to bias the electrode system 100 against the body of the user reliably.

In relation to units of the electrode system 100, the garment 102 can be configured to position the electrode system(s) 100 proximal one or more of: the pectoralisis muscles, the abdominal muscles, the oblique muscles, the trapezius muscles, the rhomboid muscles, the teres major muscles, the latissimus dorsi muscles, the deltoid muscles, the biceps muscles, and the triceps muscles when the garment 102 is worn by the user. Additionally or alternatively, the garment 102 can be configured to position the electrode system(s) 100 proximal one or more of: the gluteus maximus muscles, the gluteus medius muscles, the vastus lateralis muscles, the gracilis muscles, the semimembranosus muscles, the semitendinosis muscles, the biceps femoris, the quadriceps muscles, the soleus muscles, the gastrocnemius muscles, the rectus femoris muscles, the sartorius muscles, the peroneus longus muscles, and the adductor longus muscles when the garment 102 is worn by the user. Variations of the garment 102 can, however, be configured to position units of the electrode system 100 at the body of the user in any other suitable manner.

The information transfer inlay 104 can include one or more of: conductive, optical, or audible routing between various components. In particular, the information transfer inlay 104 can electrically, optically or audibly couple one or more components coupled to the garment 102, in order to facilitate signal transmission between the components. As such, in relation to the electrode system 100, the information transfer inlay 104 can electrically, optically or audibly couple one or more units of the electrode system 100, and couple the electrode system(s) 100 to the portable control module 106.

The information transfer inlay 104 can be integrated with (e.g., bonded into) the fabric of the garment 102. Additionally or alternatively, the information transfer inlay 104 can be manufactured individually and coupled to the garment 102 after the garment 102 is made. Further, the information transfer inlay 104 can be bonded to any type of garment 102 and need not be specific to a particular apparel type or design. In some variations, a user can customize the location of the information transfer inlay 104 based on the desired locations of one or more electrode systems 100 or one or more portable control modules 106. In relation to the information transmitted using the information transfer inlay 104, information can include any one or more of: data, signals, or other information that is transferred via the information transfer inlay 104. In specific examples, the information can include data, signals, or other information associated with movement, heart rate, respiration, or muscle activity obtained using one or more instances of the electrode system 100 described below; however, the information can additionally or alternatively comprise any other suitable information.

As discussed above, the garment 102 can be configured to couple to and/or communicate with one or more portable control modules 106. In variations, the portable control module(s) 106 can include circuitry for processing signals, storing data, and/or transmitting data, derived from signals generated using the electrode system 100, to a computing device external to the garment 102. Additionally, the portable control module 106 can include an attachment interface (e.g., mounting module) by which the portable control module 106 physically couples to the wearable garment 102 and/or by which the portable control module 106 electrically couples to the information transfer inlay 104. For example, the portable control module 106 can permanently or removably couple to the garment 102 when forming an electrical connection with the information transfer inlay 104. For instance, coupling the portable control module 106 to the garment 102 may include depositing the portable control module 106 in a mounting pocket of the garment 102 and/or otherwise electrically coupling the portable control module 106 via an interface to the information transfer inlay 104. In one example embodiment, the mounting pocket includes both physical coupling elements and electrical coupling elements that establish an electrical coupling to the information transfer inlay 104 upon the user physically coupling the portable control module 106 to the mounting pocket. For example, a portion of the information transfer inlay 104 can terminate with one or more conductive leads within the mounting pocket of the garment 102. The portable control module 106 can include embodiments, variations, and examples of the control module described in U.S. application Ser. No. 14/541,446, entitled "System and Method for Monitoring Biometric Signals" and filed on 14 Nov. 2014; however, the portable control module 106 can additionally or alternatively include any other suitable control module.

The electrode system 100 described below can thus be configured to interface with an embodiment of the garment 102, information transfer inlay 104, and/or control module 106 described in one or more of: U.S. application Ser. No. 14/541,446, entitled "System and Method for Monitoring Biometric Signals" and filed on 14 Nov. 2014, U.S. application Ser. No. 14/079,629, entitled "Wearable Architecture and Methods for Performance Monitoring, Analysis, and Feedback" and filed on 13 Nov. 2013, and U.S. application Ser. No. 14/079,621, entitled "Wearable Performance Monitoring, Analysis, and Feedback Systems and Methods" and filed on 30 Jan. 2014. However, the electrode system 100 can additionally or alternatively be configured to interface with any other suitable element(s).

1.2 System—Electrode System

As noted above, the electrode system 100 includes: a substrate 110 comprising a reference conductive region 120 and a signal communication region 130 coupled to the reference conductive region, the signal communication region 130 including a set of conductive leads 135; a set of biosensing contacts 140 coupled to the set of conductive leads 135 of the signal communication region 130; a non-conductive region 150 ensheathing each of the set of biosensing contacts; a first bonding layer 160 that couples the substrate 110 to a fabric base; and a second bonding layer 170 coupled to the first bonding layer 160, wherein the substrate 110 is sealed between the first bonding layer 160 and the second bonding layer 170.

In relation to the information transfer inlay 104 described in Section 1.1 above, one or more portions of the electrode system 100 can be integrated with the information transfer inlay 104. For instance, in one variation, the substrate 110 can be integrated with the information transfer inlay 104, such that the set of conductive leads 135 is coupled to the first bonding layer 106, and exposed for coupling to the set of biosensing contacts 140. In this embodiment, the second bonding layer 170 can thus provide a set of openings that provide access to the set of conductive leads 135 that are integrated with the information transfer inlay 104, wherein the set of openings enable coupling of the set of conductive leads 135 to the set of biosensing contacts 140. Alternative variations of integration between the information transfer inlay 106, the garment 102, and the electrode system 100 can, however, be configured in any other suitable manner.

As noted below, in relation to the manufacturing method 200, portions of the electrode system 100 can be pre-constructed, in a modular manner, prior to coupling of the electrode system 100 to a garment. For instance, the set of biosensing contacts 140 and the non-conductive region 150 can be pre-constructed prior to coupling of the set of biosensing contacts 140 to the set of conductive leads 135, in order to facilitate fabrication of the garment-based bio-signal detection system in an efficient manner. Alternatively, a non-conductive region 150 coupled to a fabric base 60, with openings (e.g., laser-cut openings) corresponding to the set of biosensing contacts 140 can be applied to fabric of the garment 102 (e.g., with a polyurethane bonding layer) over a set of conductive leads 135 of a substrate 110, and the material of the set of biosensing contacts 140 can be applied within the openings (e.g., laser-cut openings), as shown in FIGS. 14A-14C. Alternative variations of modularity in the electrode system 100 can, however, be implemented according to requirements of specific applications involving the electrode system 100.

1.2.1 Electrode System—Substrate

The substrate 110 can comprise a reference conductive region 120 and a signal communication region 130 coupled to the reference conductive region, wherein the signal communication region 130 includes a set of conductive leads 135. The substrate functions to facilitate coupling between the set of conductive leads 135 and the set of biosensing contact 140 (described in more detail below), and to enable transmission of signals from the set of conductive leads for downstream processing. The substrate is preferably flexible, but can alternatively be rigid or exhibit both flexibility and rigidity (e.g., by using a combination of rigid and flexible materials). In variations wherein the substrate no is flexible, the substrate no can be composed of a polymer material (e.g., polyamide, polyether ether ketone, etc.). In variations wherein the substrate 110 is rigid, the substrate 110 can be composed of one or more of: a rigid polymer material (e.g., a polytetrafluoroethylene based material), a rigid ceramic material (e.g., FR-4, etc.), a rigid metallic material, or a rigid semiconductor material (e.g., silicon with oxidized regions to define conductive and insulating portions of the substrate). As noted above, composite variations of the substrate can include a combination of materials, isolated to specific regions of the substrate no, that provide regions of flexibility and regions of rigidity. Additionally or alternatively, materials used in the substrate 110 can be configured to provide flexibility in certain environmental conditions and rigidity in other environmental conditions. In a specific example, the substrate 110 can comprise a flexible printed circuit board (PCB); however, variations of the specific example can alternatively comprise any other suitable component.

The reference region 120 of the substrate 110 functions to serve as a reference "plane", by which noise and/or any static charge, resulting from motion of the user during performance of a physical activity, can be dissipated. The reference region 120 thus functions to facilitate sensing of low amplitude biopotential signals, which can be lost or difficult to pars from environmental noise and/or noise produced by the body of the user. As such, the reference region 120 is preferably a layer of the substrate no, wherein the layer can be configured to completely cover the areas directly over the portion of the electrode system 100 where biometrical signals of the user are measured through the set of biosensing contacts 140. However, the reference region 120 can alternatively not be configured as a layer, and/or can be configured relative to other elements of the electrode system 100 in any other suitable manner.

Preferably, the reference region 120 is coupled to the garment 102, in order to reduce an amount of static due to motion of the garment 102 relative to the set of biosensing contacts 140 of the electrode system 100; however, the reference region 120 can alternatively be configured relative to other portions of the system 100 in any other suitable manner. In particular, signal noise/interference can result from any one or more of: motion of the electrode system 100 relative to the garment 102, the body of the user (e.g., skin of the user), motion of the electrode system 100 and/or garment relative to additional pieces of clothing worn by the user, and any other suitable source. The reference region 120 can thus provide a region (e.g., surface area) across which any static can dissipate before the static develops an interference signal that reduces signal quality downstream, during signal processing.

In addition, for variations in which the reference region 120 functions as a reference shield, the reference region 120 can provide a region of material configured between the set of biosensing contacts 140 and the garment 102, in order to shield sensitive contact points of the set of biosensing contact 140 from friction, static, and other noise sources that the garment 102 produces relative to other surfaces. As such, the reference region 120 can provide an electrostatic barrier between the set of biosensing contacts 140 and the garment 102. In particular, in situations wherein a user wears additional clothing over the garment 102, additional static and/or noise can be produced due to the garment 102 and additional clothing rubbing together. Thus, the reference region 120 can dissipate some or all of the resulting static preventing static transfer to other portions of the electrode system 100.

Additionally or alternatively, to dissipate static charges and shield the biosensing site of the user where the biometric signals are measured, at least a portion of the reference region 120 can be connected to the user at a superficial portion of the electrode system 100 (e.g. at a portion of the electrode system 100 away from the biosensing contacts that contact the skin of the user).

Figure 2A:
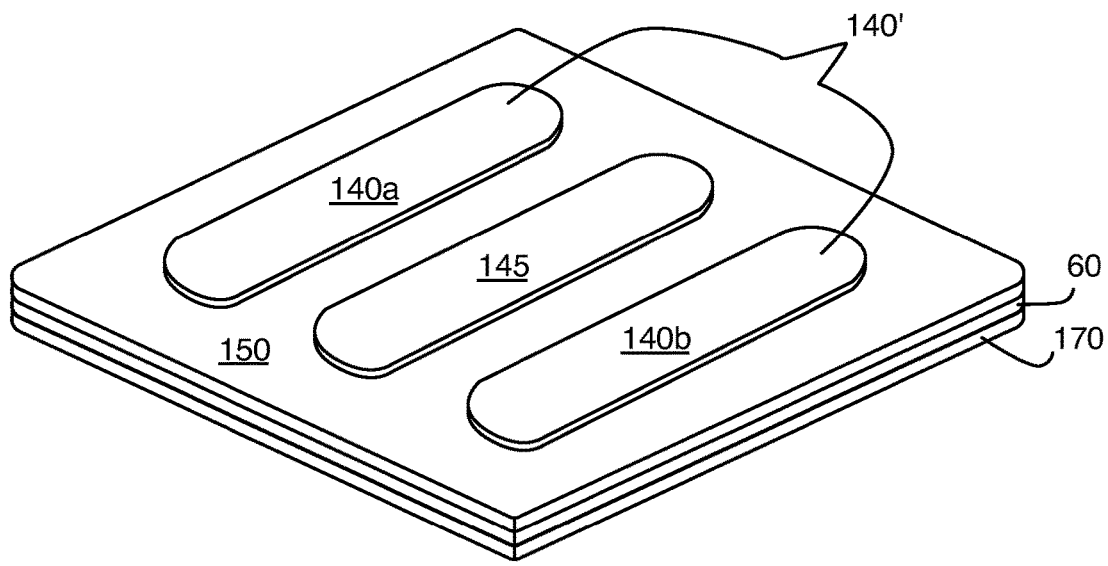
FIGS. 2A and 2B depict a variation of a portion of an electrode system.
Figure 2B:
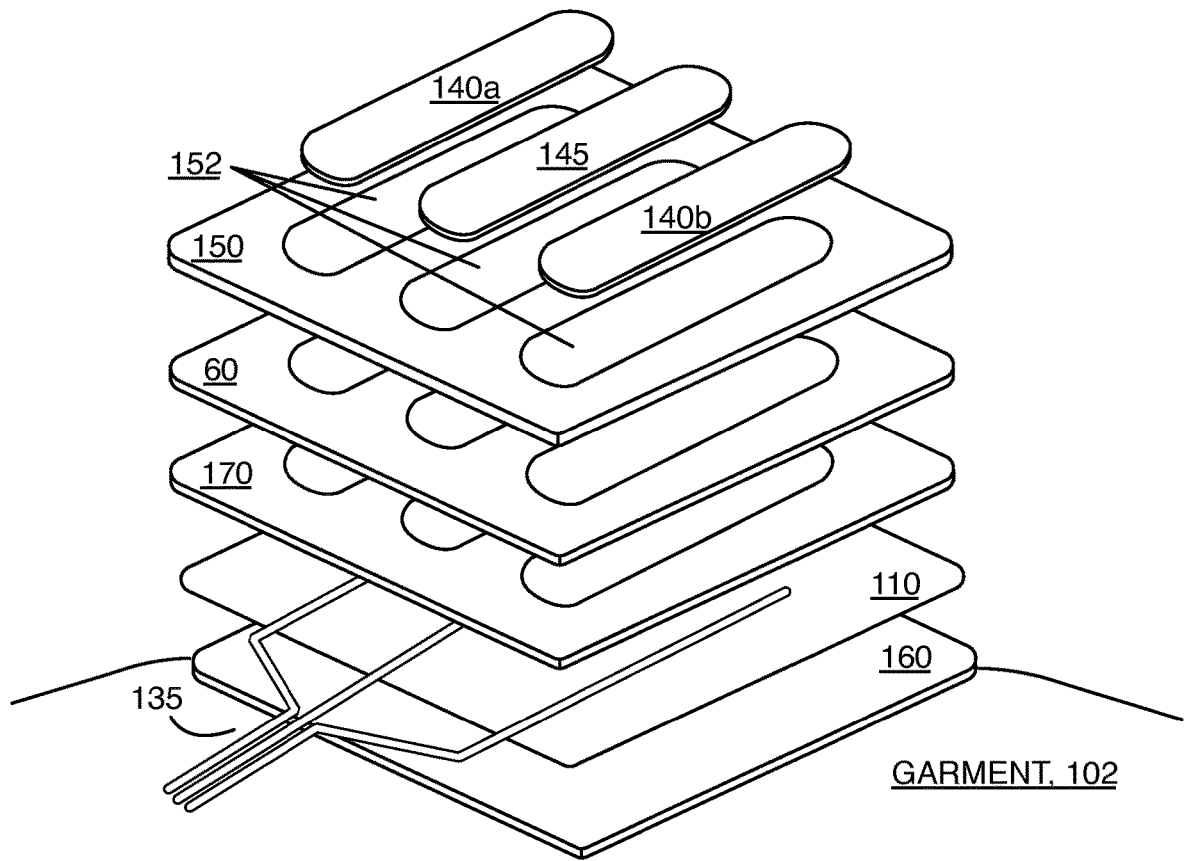
Figure 3A:
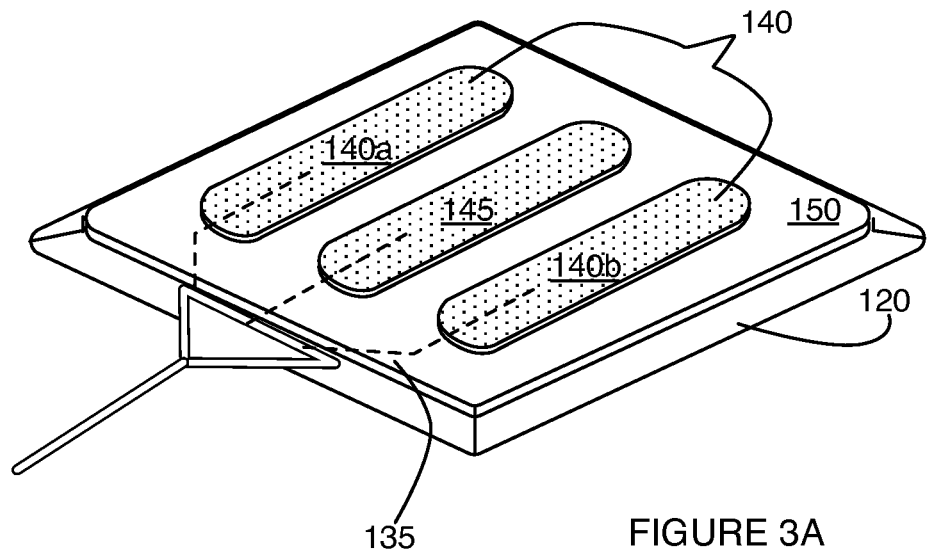
FIGS. 3A and 3B depict a variation of a portion of an electrode system.
Figure 3B:
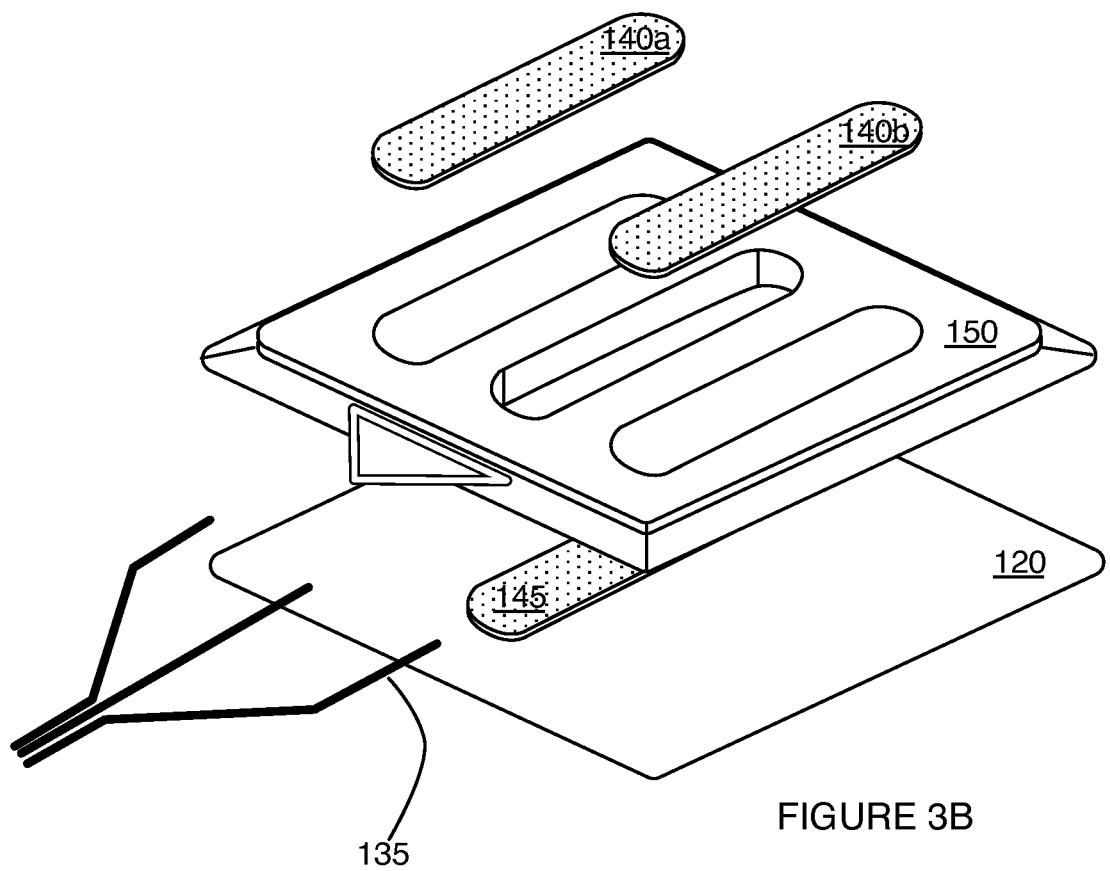
Figure 4:
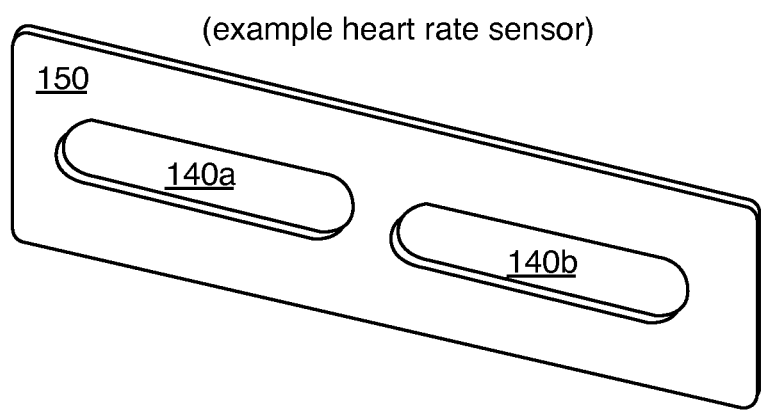
FIG. 4 depicts a variation of a portion of an electrode system.

The reference region 120 can additionally or alternatively serve to enable detection and removal of a common-mode component of noise (e.g., 60 Hz noise) from the body of the user, in order to enhance signal processing of biopotential signals received at the set of biosensing contacts 140. As such, the reference region 120 can couple to a reference contact 145, configured to interface with the body of the user when the garment 102 is worn by the user, wherein the reference contact enables detection of the common-mode component of noise (e.g., 60 Hz noise, noise due to motion of the electrode on the skin of the user). In one variation, in relation to the set of biosensing contacts 140 described below, the reference contact 145 can be configured between a pair of biosensing contacts, as shown in FIGS. 2A and 2B, such that the reference contact 145 is equidistant from each biosensing contact in the pair of biosensing contacts. As such, in relation to a differential biosignal measurement from the pair of biosensing contacts, the reference contact 145 can enable detection of a component of 60 Hz noise or noise due to motion of the electrode system 100 relative to the user's skin, in order to facilitate downstream signal processing. In particular, due to proximity between the set of biosensing contacts 140 and the reference contact 145, noise present in any detected signals from each of the set of biosensing contacts 140 can be substantially similar to the noise detected within a reference signal by the reference contact 145. Furthermore, in configurations wherein the reference contact 145 is substantially equidistance from each of a set biosensing contacts 140 the signals received from each of the set of biosensing contacts 140 can be equally related to the reference signal from the reference contact 145. In one or more variations, the reference signal that the reference contact 145 detects can be used to filter, subtract, or otherwise eliminate the noise found in the signals from the set of biosensing contacts 140. Therefore, the reference signal can provide, when used in combination with signals from the set of biosensing contacts 140, a more accurate reading of any measurement derived from the electrode system 100.

Additionally or alternatively, the electrode system 100 can cooperate with a reference contact 145 separate from the electrode system 100, wherein the reference contact 145 is configured to detect a component of 60 Hz noise from a body region of the user (e.g., a body region away from the body region with which the electrode system interfaces) wherein the component of 60 Hz noise is used during signal processing to cancel noise associated with a biosensing contact. As such, variations of the substrate 100 can alternatively omit the reference region 120 and/or a reference contact 145, for instance, due to inclusion of a shared reference region 120/reference contact 145 for multiple units of the electrode system 100. Additional variations of the configurations of the reference contact 145 relative to biosensing contacts are shown in FIGS. 3A, 3B, 4, and 5, and described further below in relation to the set of biosensing contacts 140.

The signal communication region 130 is coupled to the reference region 120 of the substrate 110, and functions to couple the set of biosensing contacts 140 to a set of conductive leads 135, for signal transmission to other elements in communication with the electrode system 100. As such, the signal communication region 130 is preferably a layer of the substrate 110, wherein the layer is configured between the layer comprising the reference region 120 and the region defined by the set of biosensing contacts. However, the signal communication region 130 can alternatively not be configured as a layer, and/or can be configured relative to other elements of the electrode system 100 in any other suitable manner.

As noted above, the signal communication region 130 includes a set of conductive leads 135 configured to couple to the set of biosensing contacts 140 (described in further detail below), and configured to enable signal transmission from the set of biosensing contacts 140, through the information transfer inlay 104, and to a portable control module 106. As such, the set of conductive leads 135 functions to provide signal routing pathways from the set of biosensing contacts 140, to a portable control module 106. The set of conductive leads 135 is preferably defined at a broad surface of the substrate 110 configured to face skin of the user, when the garment 102 is worn by the user. However, the set of conductive leads 135 can alternatively be situated at any other suitable region of the substrate 130, with coupling between the set of conductive leads 135 and the set of biosensing contacts 140 implemented in any other suitable manner. Furthermore, each conductive lead in the set of conductive leads 135 is preferably composed of a metallic material that is electrically conductive; however, the set of conductive leads 135 can additionally or alternatively include any other suitable conductive material (e.g., conductive polymer, etc.).

Figure 7A:
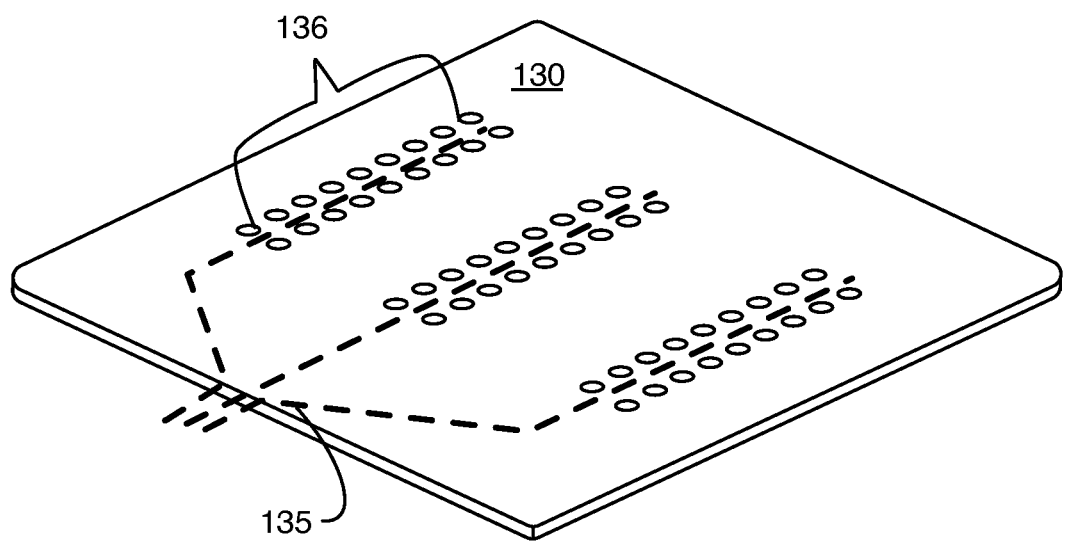
FIGS. 7A-7D depict variations of a portion of an electrode system, comprising a set of conductive leads.
Figure 7B:
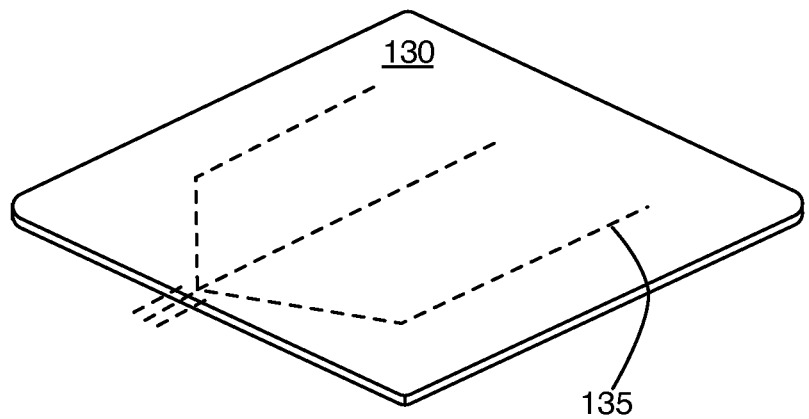
Figure 7C:
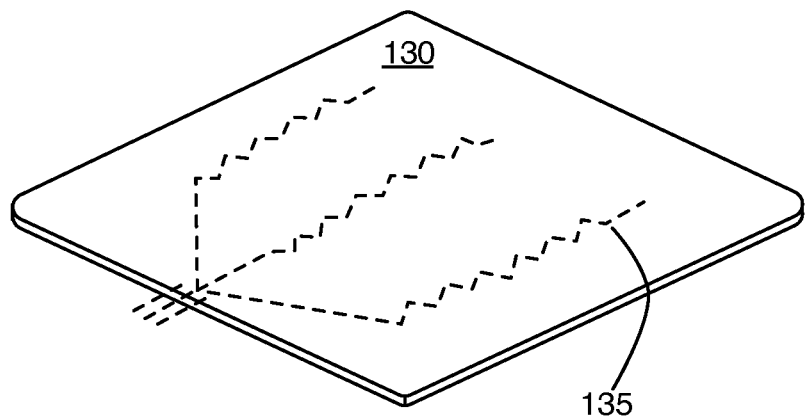
Figure 7D:
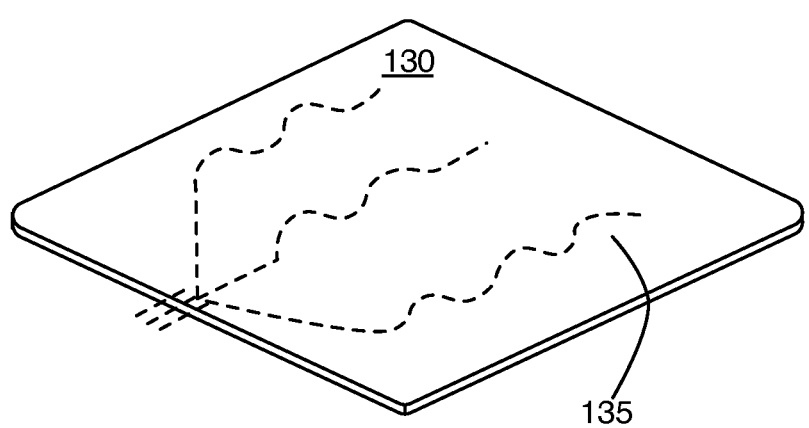

In coupling the set of conductive leads 135 to the signal communication region 130 of the substrate no, one or more of: an embroidery method, a conductive epoxy, a crimping method, a soldering method, a laser direct structuring approach, a two-shot molding approach, screen printing approach and any other suitable method can be used to couple the set of conductive leads 135 to the signal communication region 130. In one specific example, the set of conductive leads 135 comprises copper leads coupled to the substrate 110 at the signal communication region 130. In additional specific examples, as shown in FIGS. 7B-7D, the set of conductive leads 135 can comprise conductive thread embroidered into a surface of the signal communication region 130, wherein the conductive thread is initially exposed to enable coupling of the set of biosensing contacts 140 to the conductive thread. The conductive thread can have a defined stitching pattern that increases surface area contact of the conductive thread with a biosensing contact of the set of biosensing contacts 140. In variations of these examples, the stitching pattern can be one or more of: serpentine, zig-zagged, linear, curved, and crossed. However, the conductive thread can additionally or alternatively comprise any other suitable stitching pattern and/or be coupled to the signal communication region 130 of the substrate no in any other suitable manner.

In relation to coupling of the signal communication region 130 of the substrate no to the set of biosensing contacts 140 (described in more detail below), The substrate 110 can include one or more features that enhance coupling of the set of biosensing contacts 140 to the signal communication region 130, proximal the set of conductive leads 135. In a first variation, as shown in FIG. 7A, the substrate no includes a plurality of openings 136, proximal the set of conductive leads 135, configured to provide additional surface area to increase the peel strength between the set of biosensing contacts 140 and the signal communication region 130 of the substrate no. Additionally or alternatively, the plurality of openings 136 in the substrate no can provide bonding points between the substrate no and the garment 102, as described in relation to the bonding layers 160, 170 of Section 6.2.4 below. In particular, when bonding the substrate no of the electrode system 100 to the garment 102, material of a bonding layer 160, 170 can flow through the plurality of openings 136 in the substrate no and strengthen a bond between the substrate 110 and the garment 102. Additionally, the plurality of openings 136 can increase flexibility of the substrate 110 in response to bending and/or torsional stresses experienced during use.

Additionally or alternatively, in a second variation, the substrate 110 can comprise a set of recesses in order to provide additional surface area to increase the peel strength between the set of biosensing contacts 140 and the signal communication region 130 of the substrate 110. Additionally or alternatively, in a third variation, the substrate no can comprise an abraded surface in order to provide additional surface area to increase the peel strength between the set of biosensing contacts 140 and the signal communication region 130 of the substrate 110. Additionally or alternatively, in a fourth variation, an adhesive primer can be applied to a surface of the substrate 110 prior to coupling of the set of biosensing contacts 140 to the signal communication region 130 of the substrate. The regions of the substrate no proximal the signal communication region 130 can, however, be configured in any other suitable manner to facilitate coupling between the signal communication region 130 and the set of biosensing contacts 140.

1.2.2 Electrode System—Biosensing Contacts

The set of biosensing contacts 140 functions to detect signals from a body region of the user, when the garment 102 is worn by the user. As such, the set of biosensing contacts 140 is configured to be coupled to the set of conductive leads 135 of the signal communication region 130, and configured to interface with skin of the user when the garment 102 is worn by the user, such that signals from the body of the user can be transmitted through the set of conductive leads 135 for downstream processing, by way of the portable control module 106.

The set of biosensing contacts 140 is preferably composed of a conductive polymer material, which can be delivered to the signal communication region 130 of the substrate no in a flow state, and transitioned to a set state (e.g., after curing). Variations of methods for forming the set of biosensing contacts 140 at the substrate no are described further in Section 2 below. In a specific example, the set of biosensing contacts 140 is composed of a conductive silicone material, which readily bonds to non-conductive silicone used to form the non-conducting region 150, as described in further detail below; however, alternative variations of the set of biosensing contacts 140 can alternatively be composed of any other suitable material that readily couples to other related portions of the electrode system 100.

In some variations, the set of biosensing contacts 140 comprises biosensing contacts configured to generate a differential biopotential measurement, to generate a differential biopotential measurement relative to a reference contact, to generate a differential biopotential measurement in cooperation with a reference shield (i.e., for static dissipation), or to generate any suitable number of single ended measurements (e.g., with two non-paired biosensing contacts, with three non-grouped biosensing contacts, etc.). Each biosensing contact in the set of biosensing contacts 140 can be identical in morphology to the other biosensing contacts, or alternatively, the set of biosensing contacts 140 can comprise contacts having different morphologies. A biosensing contact can be one or more of: circular, ellipsoidal, polygonal, and amorphous in footprint, and can protrude from a surface of the electrode system 100 with a suitable height that allows the biosensing contact to interface with skin of the user during use. Alternatively, one or more of the set of biosensing contacts 140 and/or reference contact 145 can be substantially flush with a surface of the non-conductive region 150 (described below), in a manner that still allows for contact with skin of the user during use. In relation to the set of biosensing contacts 140, the set of biosensing contacts 140 can be uniformly spaced across a broad surface of the signal communication region 130 of the substrate no, can be arranged in an array (e.g., rectangular array, circular array, ellipsoidal array, etc.) at the broad surface of the substrate 110, or can alternatively be arranged in any other suitable configuration. In specific examples, as shown in FIGS. 2A-6, each biosensing contact 140 in the set of biosensing contacts 140 has an ellipsoidal footprint, and the set of biosensing contacts 140 is arranged as a uniformly spaced linear array.

Figure 5:
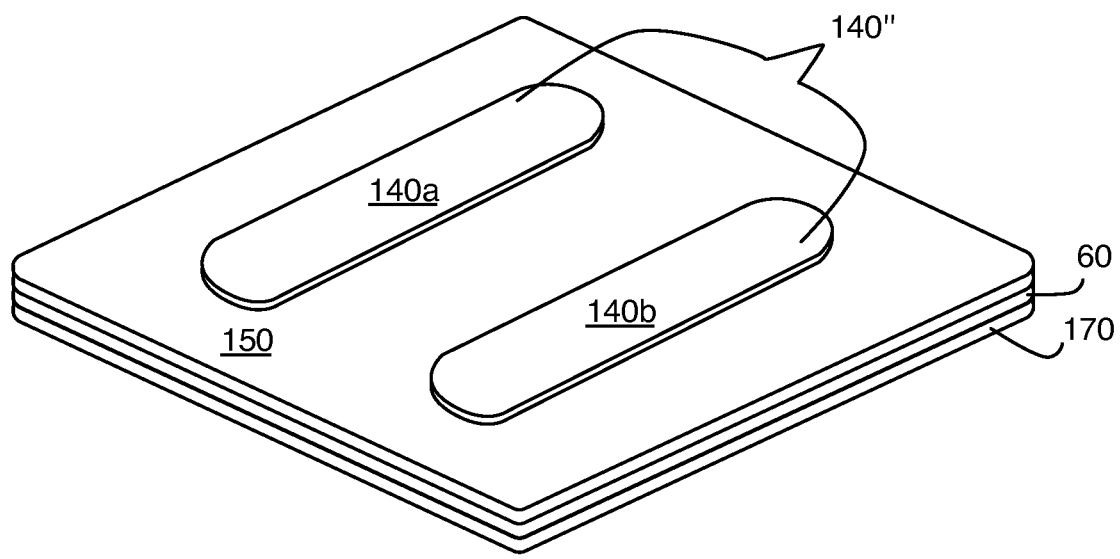
FIG. 5 depicts a variation of a portion of an electrode system.

In a first set of variations, an example of which is shown in FIG. 5, the set of biosensing contacts 140 can include paired biosensing contacts that can enable differential measurement of a biosignal from the body of the user. In the first set of variations, the electrode system 100 can include a pair of biosensing contacts including a first biosensing contact 140a and a second biosensing contact 140b. In particular, the first biosensing contact 140a can detect a first biopotential signal and the second biosensing contact 140b can detect a second biopotential signal. The electrode system 100 can then provide the first biopotential signal and the second biopotential signal to the portable control module 106, by way of the information transfer inlay 104. The portable control module 106 and/or other computing device can then use the first biopotential signal and the second biopotential signal to determine a composite signal associated with a differential biopotential measurement (e.g., electrocardiogram or electromyography signal).

In a second set of variations, examples of which are shown in FIGS. 2A-3B, the set of biosensing contacts 140' can include paired biosensing contacts that can enable differential measurement of a biosignal from the body of the user. Similar to the first set of variations, the electrode system 100 of the second set of variations can include a pair of biosensing contacts including a first biosensing contact 140a and a second biosensing contact 140b. Furthermore, as noted in relation to the reference region 120 of the substrate 110, the first biosensing contact 140a and the second biosensing contact 140b can surround (i.e., be adjacent to, oppose each other on different sides of) a reference contact 145, coupled to the reference region 120. As such, the reference contact 145 can be centered between the first biosensing contact 140a and the second biosensing contact 140b and be in communication with the reference region 120, while the first and the second biosensing contacts 140a, 140b communicate with the signal communication region 140 by way of the set of conductive leads 135. As such, the electrode system 100 can then provide the first biopotential signal and the second biopotential signal, as well as a reference signal from the reference contact 145 to the portable control module 106, by way of the information transfer inlay 104, to facilitate performance of downstream signal processing. As such, the portable control module 106 can sample a signal from the reference contact 145 to facilitate analysis of biopotential signals from the system 100.

In a third set of variations similar to the second set of variations, the set of biosensing contacts 140 can include paired biosensing contacts that can enable differential measurement of a biosignal from the body of the user. Similar to the first set of variations, the electrode system 100 of the second set of variations can include a first biosensing contact 140a and a second biosensing contact 140b. Furthermore, as noted in relation to the reference region 120 of the substrate no, the first biosensing contact 140a and the second biosensing contact 140b can be configured relative to an electrode contact in communication with a reference contact 145 configured to interface with the body of the user, wherein the reference contact 145 may or may not be directly coupled to the substrate no. As such, the electrode contact in communication with the reference contact 145 can be configured relative to the first biosensing contact 140a and the second biosensing contact 140b in any suitable manner. Furthermore, in this set of variations, the reference contact 145 can be in communication with multiple units of the electrode system 100, in facilitating removal of common-mode noise from the body of the user. As such, the electrode system 100 can then provide the first biopotential signal and the second biopotential signal, as well as a reference signal from a common reference contact 145 to the portable control module 106, by way of the information transfer inlay 104, to facilitate performance of downstream signal processing. As such, the portable control module 106 can sample a signal from the reference contact 145 to facilitate analysis of biopotential signals from the system 100.

In a fourth set of variations similar to the third set of variations, the set of biosensing contacts 140 can include paired biosensing contacts that can enable differential measurement of a biosignal from the body of the user. Similar to the first set of variations, the electrode system 100 of the second set of variations can include a first biosensing contact 140a and a second biosensing contact 140b. Furthermore, as noted in relation to the reference region 120 of the substrate no, the first biosensing contact 140a and the second biosensing contact 140b can be configured relative to a reference contact 145 that interfaces with a reference shield of the substrate no, wherein the reference shield facilitates mitigation of static interference. As such, the electrode contact in communication with the reference contact 145 can be configured relative to the first biosensing contact 140a and the second biosensing contact 140b in any suitable manner. As such, the electrode system 100 can provide the first biopotential signal and the second biopotential signal, to the portable control module 106, by way of the information transfer inlay 104, to facilitate performance of downstream signal processing.

Figure 6:
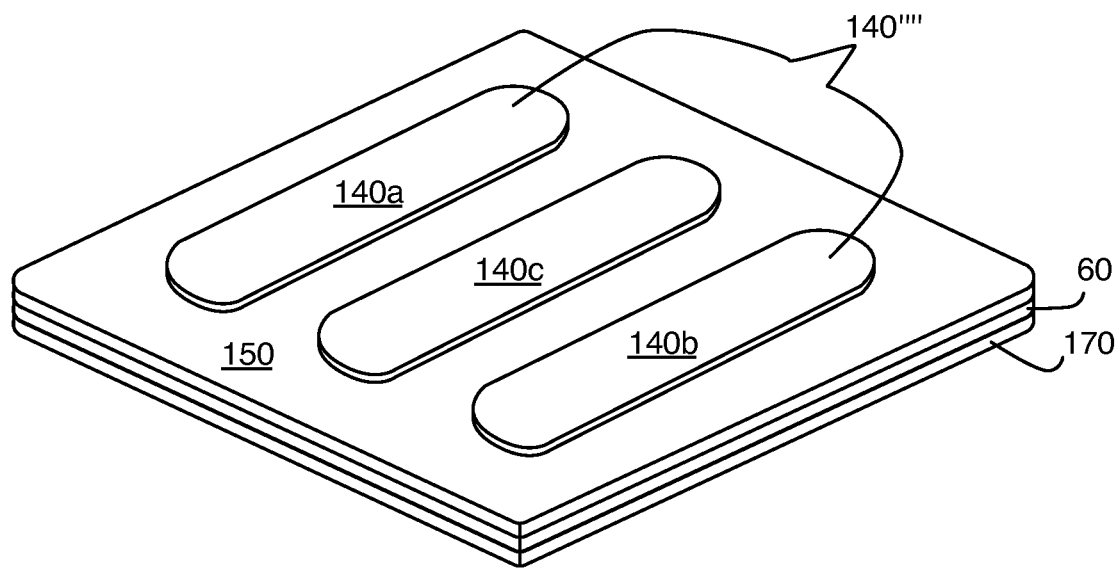
FIG. 6 depicts a variation of a portion of an electrode system.

In a fifth set of variations, the set of biosensing contacts 140"" can include two biosensing contacts, as shown in FIG. 5, wherein each of the set of biosensing contacts 140"" enables generation of a single-ended measurement (e.g., a non-paired measurement). Alternatively, in the fifth set of variations, the set of biosensing contacts 140"" can include three biosensing contacts, as shown in FIG. 6, wherein each of the set of biosensing contacts 140"" enables generation of a single-ended measurement (e.g., a non-paired measurement). As such, the electrode system 100 can provide each of the single ended measurements from the biosensing contacts, to the portable control module 106, by way of the information transfer inlay 104, to facilitate performance of downstream signal processing.

Additionally or alternatively, in one or more variations, the electrode system 100 can have different configurations of the set of biosensing contacts 140 for detecting different types of biopotential signals. In particular, a subset of the set of biosensing contacts 140 can be configured to capture a particular type of biometric or movement data (e.g., muscle activity, heart activity). Additionally or alternatively, one or more of the set of biosensing contacts 140 can include different surface areas and/or levels of sensitivity (e.g., based upon conductivity of the material used in the contact) according to features of a particular type of biometric signal. As such, in some variations, the electrode system 100 can include one or more different types of contacts for detecting different types of biometric signals. Variations of the set of biosensing contacts 140 can, however, include any suitable combination of any of the above described variations. Furthermore, the set of biosensing contacts 140 can be configured relative to a reference contact 145 in any other suitable manner.

1.2.3 Electrode System—Non-Conductive Region

The non-conductive region 150 is configured to ensheath each of the set of biosensing contacts 140 and, if present, a reference contact 145. The non-conductive region 150 thus functions to isolate each of the set of biosensing contacts 140 and/or reference contact 145, in order to prevent any undesired effects due to bridging of contacts 140, 145. The non-conductive region 150 can additionally or alternatively function to promote maintenance of coupling between the set of biosensing contacts 140 and the body of the user. Even further, the non-conductive region 150 can function to provide additional mechanical reinforcement, in preventing flexing of the substrate 110 (in variations wherein the substrate 110 is flexible).

The non-conductive region 150 is preferably configured as a layer of non-conductive material that is directly coupled to at least one of: the signal communication region 130 of the substrate 110 and a fabric patch 60 (in relation to the bonding layers 160, 170 below), wherein the signal communication region 130 and/or the fabric patch 60 are configured to couple to the garment 102 by way of at least one of the first bonding layer 160 and the second bonding layer 170. As such, openings within the non-conductive region 150 enable coupling of the set of biosensing contacts 140 to the set of conductive leads 135 of the signal communication region 130. In variations, the non-conductive region 150 can thus include a set of openings 152 that expose at least a portion of each of the set of biosensing contacts 140 and/or a reference contact 145, for interfacing with the body region of the user. Additionally or alternatively, in relation to promoting coupling between contacts 140, 145 and the body the user, the non-conductive region 150 can include a surface feature 157 configured to enhance coupling of the set of biosensing contacts to skin of the user, upon coupling of the electrode system 100 to the user.

The non-conductive region 150 is preferably composed of a non-conductive polymer material (e.g., silicone) that readily bonds or otherwise couples to the material of the set of biosensing contacts 140. Alternatively, the non-conductive region 150 can be composed of any other suitable insulating material that is processable to isolate each of the set of contacts 140, 145, as described in the method 200 of Section 2 below. In some variations, described further in the method 200 of Section 2 below, the non-conductive region 150 can be overmolded onto the substrate 110 or directly coupled to another portion of the system 100 (e.g., a fabric base 60), and the set of biosensing contacts 140 can be formed (e.g., stenciled) into a corresponding set of openings 152 of the non-conductive region 150 in a multi-step process. Alternatively, the set of biosensing contacts 140 can be coupled to the substrate 110, and the non-conductive region 150 can be coupled to the substrate 110 around the set of biosensing contacts 140 in a multi-step process. The biosensing contacts 140 and the non-conductive region 150 can, however, be coupled to their respective regions of the substrate 110/fabric patch 60 in any other suitable manner.

In relation to the set of openings 152 of the non-conductive region 150, the number of openings in the set of openings 152 preferably matches the number, morphology, and configuration of signal conducting contacts 140, 145. As such, in relation to the first through the fifth variations of the set of biosensing contacts 140 described above, the set of openings 152 of the non-conductive region 150 can include three openings, as shown in FIG. 2B. In particular, in these variations, each of the three openings can have an associated reference contact 145 or a biosensing contact of the set of biosensing contacts 140. In a first example, a first biosensing contact 140 can be coupled within a first opening 152a of the non-conductive region 150, a second biosensing contact can fit within a second opening 152b of the non-conductive region 150, and a reference contact 145 can fit within a third opening 152c (e.g., an opening positioned between the first opening 152a and the second opening 152b). In particular, the openings 152a, 152b corresponding to the set of biosensing contacts 140 can provide access to the set of conductive leads 135 of the signal communication region 130 of the substrate 110, while the opening 152c corresponding to a reference contact 145 can provide access to the reference region 120 of the substrate 110.

In an alternative example, a first biosensing contact 140 can be coupled within a first opening 152a of the non-conductive region 150, a second biosensing contact can fit within a second opening 152b of the non-conductive region 150, and a third biosensing contact can fit within a third opening 152c of the non-conductive regions 150. In an example wherein the set of biosensing contacts 140 includes two biosensing contacts (and the electrode system 100 does not include a reference contact), a first biosensing contact 140 can be coupled within a first opening 152a of the non-conductive region 150, a second biosensing contact can fit within a second opening 152b of the non-conductive region 150. In particular, the openings 152a, 152b corresponding to the set of biosensing contacts 140 can provide access to the set of conductive leads 135 of the signal communication region 130 of the substrate 110.

In some variations, as noted above, the non-conductive region 150 can include a surface configured to enhance coupling of the set of biosensing contacts to skin of the user, upon coupling of the electrode system 100 to the user. In variations, the surface can increase surface tack and/or friction with skin of a user, such that the set of biosensing contacts 140 is substantially retained in position at a desired body region of the user. In particular, a surface of the non-conductive region 150 that faces the body of the user during use can be composed of a material having high surface tack that limits motion of the signal conducting contacts 140, 145 during use. In one example, the non-conductive region 150 can include a non-conductive silicone material that maintains substantially constant contact with a surface of the skin and has a high surface tack, such that the non-conductive region 150 does not slide along a surface of the skin while the user performs an activity. Additionally or alternatively, the signal conducting contacts 140, 145 can have a surface feature 157 similar to that of the non-conductive region 150 configured to increase surface tack and/or friction with skin of a user, thereby further promoting coupling of the set of biosensing contacts to skin of the user in a reversible manner, without any adhesive (e.g., hydrogel adhesive material).

In addition to using a material that increases surface tack between the electrode system 100 and skin of a user, one or more of: the non-conductive region 150, the reference contact 145, and each of the set of biosensing contacts 140 can include a surface feature 157 that contacts the skin of the user. The surface feature 157 can additionally function to provide more reliable electrical contact between the signal conducting contacts 140, 145 and skin of the user through hair, sweat, and/or other obstructions that may interfere with maintaining a reliable connection between the electrode system 100 and skin of a user. In particular, the surface feature 157 can include one or more morphological features and/or textures that engage the user's skin. In variations, the surface feature 157 can include one or more of: protrusions, bumps, grooves, non-planar surfaces compliant to a body region of the user, and any other suitable surface feature that engage the user's skin and promote maintenance of contact with the user's skin.

Figure 8A:
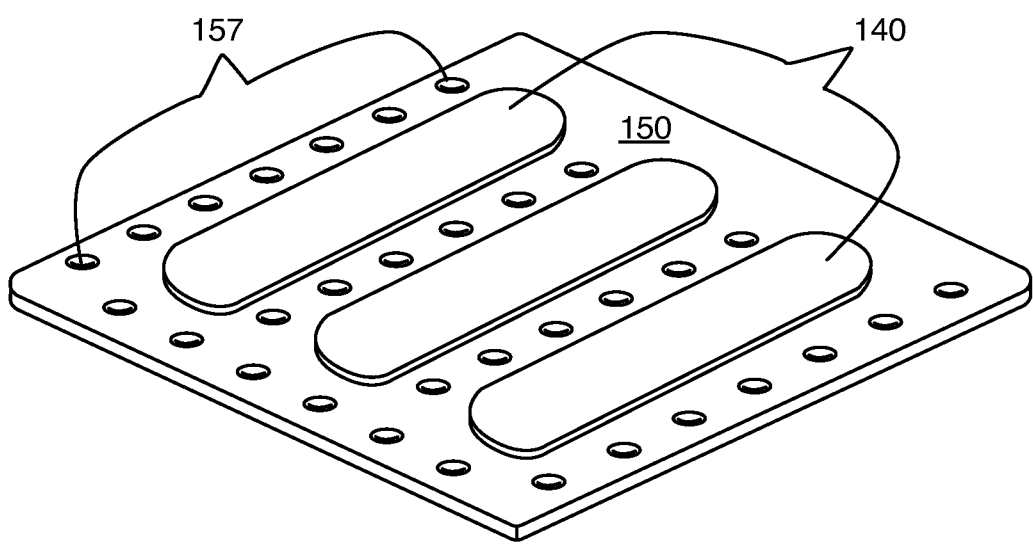
FIGS. 8A-8B depict variations of a portion of an electrode system, comprising a surface feature.

In one example, shown in FIG. 8A, a surface feature 157 at a surface of the non-conductive region 150 can include a movement reduction pattern configured at a peripheral region of the non-conductive region 150, surrounding the set of biosensing contacts 140. In this example, the movement reduction pattern can include at least one morphological feature (e.g., protrusion) that is able to move relative to the non-conductive region 150 as the fabric of the garment 102 is strained and stressed as a result of motion of the user. In more detail and as shown in FIG. 8A, the surface feature 157 can include a plurality of non-conductive dot protrusions arranged in an array about the set of biosensing contacts 140, which are able to move relative to each other in relation to stretching of the fabric base of the garment 102. Thus, the dot protrusion features can function to reduce motion or movement of the electrode system 100 relative to the user during use. In alternative variations to the specific example, any other suitable surface feature 157 can be positioned about the signal conducting contacts 140, 145. For example, instead of dot protrusion features, the surface feature(s) 157 can include one or more patterns (e.g., linear patterns) of non-conductive material, or other shaped extensions from the fabric that interact with the skin of the user to prevent movement of the area of the garment corresponding to the biometric electrode.

Figure 8B:
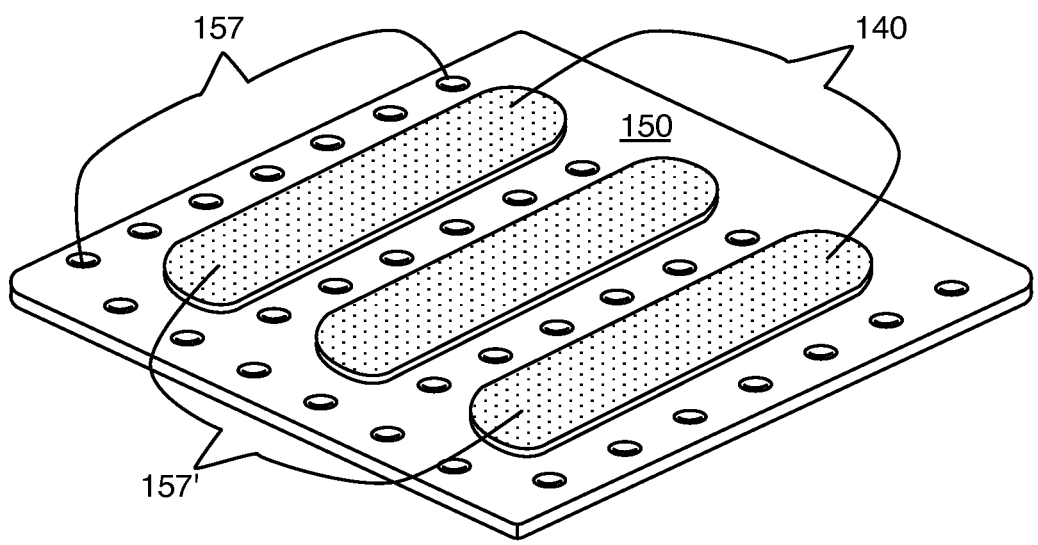

In another example shown in FIG. 8B, the reference contact 145 and each of the set of biosensing contacts 140 can include a plurality of protrusions 157' at a surface of the contact that comes into contact with the skin.

Figure 9:
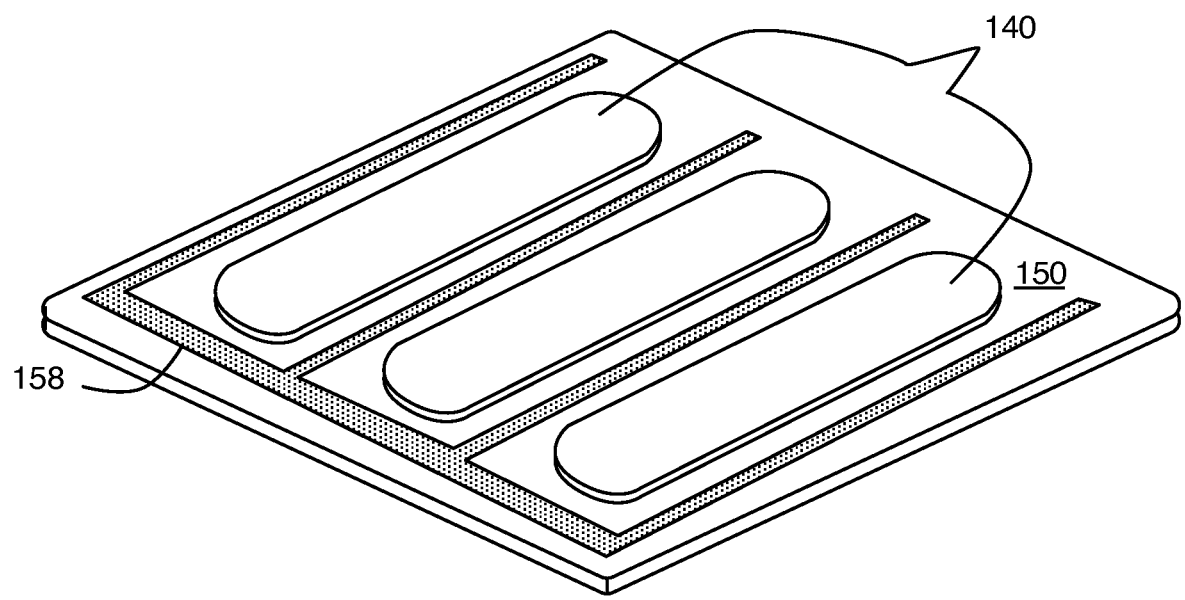
FIG. 9 depicts a variation of a portion of an electrode system, comprising a barrier.

In some variations, the non-conductive region 150 can include or be coupled to a feature that either functions as a barrier against bridging of contacts 140, 145 (e.g., by sweat generated during an activity of the user), or that functions to divert any present fluid in a controlled manner, to prevent bridging of contacts. In one such variation, as shown in FIG. 9, the non-conductive region 150 can be coupled to a barrier 158 of a porous material (e.g., porous foam) configured between the reference contact 145 and each of the set of biosensing contacts 140, wherein the barrier 158 prevents sweat or other moisture from bridging the contacts 140, 145 and causing a low resistance path between the contacts 140, 145. The porous material of the barrier 158 can readily absorb excess moisture that could otherwise create a secondary conductive path between the contacts 140, 145 in an undesired manner. In an alternative to this example, the barrier 158 can additionally or alternatively function to divert any fluid in proximity to the contacts 140, 145, away from the contacts 140, 145 by providing a low resistance fluid path away from the contacts 140, 145.

1.2.4 Electrode System—Bonding Layers

The first bonding layer 160 is configured to couple the substrate 110 (e.g., integrated with the information transfer inlay 104) to fabric of a garment 102, and functions to form a first portion of a bonding assembly that seals sensitive portions of the substrate 110 (e.g., integrated with the information transfer inlay 104) from damage or shorting that could otherwise result from fluid reaching the substrate 110. As such, the first bonding layer 160 can facilitate isolation of one or more of: the reference region 120 of the substrate 110, the signal communication region 130 of the substrate 110, and the set of conductive leads 135 from fluid (e.g., sweat) associated with a period of physical activity performed by the user. In one variation, as shown in FIGS. 1 and 2B, the first bonding layer 160 can couple a flexible variation of the substrate no to fabric of the garment 102, thus forming a first portion of an assembly that seals the substrate 110 from moisture.

The first bonding layer 160 is preferably composed of a hydrophobic material that is impermeable to fluids; however, the material of the first bonding layer 160 can alternatively be non-hydrophobic while still being impermeable to fluids. In a specific example, the first bonding layer 160 comprises a polyurethane film that can be thermally bonded to the second bonding layer 170 and/or other elements of the system 100; however, variations of the first bonding layer 160 can be composed of any other suitable material (e.g., polymeric material) that is bondable to other elements of the system 100 in any other suitable manner (e.g., by adhesive bonding, etc.). Furthermore, in order to enhance the strength of bonding between the first bonding layer 160 and the second bonding layer 170, the first and the second bonding layers 160, 170 are preferably composed of identical materials; however, in alternative variations, the first and the second bonding layers 160, 170 can alternatively be composed of different materials.

The second bonding layer 170 is configured to couple to at least a portion of the first bonding layer 160, such that the substrate 110 is sealed between the first bonding layer 160 and the second bonding layer 170. As such, in one variation, the second bonding layer 170 can be coupled to the first bonding layer 160 at a peripheral region of the first bonding layer, to seal the substrate 110 within the bonding layers 160, 170. In this variation, as shown in FIG. 2B, a first surface of the second bonding layer 170 is configured to couple to the substrate 110 and the first bonding layer 160, while a second surface of the second bonding layer 170 that opposes the first surface is configured to couple to a fabric patch 60, to which the non-conductive region 150 is coupled. As such, in this variation, openings in the fabric patch 60 and the second bonding layer 170 can provide access to the set of conductive leads 135 of the substrate 110, when the material of the signal conducting contacts 140,145 is transmitted toward the set of conductive leads 135. In this variation, the second bonding layer 170, the fabric patch 60, and the non-conductive region 150 can thus comprise an initial assembly that is coupled to the first bonding layer 160 at the garment. Then, the signal conducting contacts 140, 145 can be coupled to the set of conductive leads 135 by way of the set of openings 152 of the non-conductive region 150 that pass through the fabric patch 60 and the second bonding layer 170. In this variation, fabric that does not interfere with signal conduction by the signal conducting contacts 140, 145 can be provided in any suitable manner, thus providing material that increases comfort when the electrode system 100 interfaces with the user. However, similar variations may omit fabric, such that no fabric layer covers the second bonding layer 170.

The second bonding layer 170 is preferably composed of a hydrophobic material that is impermeable to fluids; however, the material of the second bonding layer 170 can alternatively be non-hydrophobic while still being impermeable to fluids. In a specific example, the second bonding layer 170 comprises a polyurethane film that can be thermally bonded to the first bonding layer 160 and/or other elements of the system 100; however, variations of the second bonding layer 170 can be composed of any other suitable material (e.g., polymeric material) that is bondable to other elements of the system 100 in any other suitable manner (e.g., by adhesive bonding, etc.). Furthermore, in order to enhance the strength of bonding between the first bonding layer 160 and the second bonding layer 170, the first and the second bonding layers 160, 170 are preferably composed of identical materials; however, in alternative variations, the first and the second bonding layers 160, 170 can alternatively be composed of different materials.

In a specific example, the substrate 110 is bonded to the fabric base 60 of the garment 102 using a first bonding layer 160 comprising polyurethane film. In particular, in the specific example, the first bonding layer 160 is applied to the substrate 110 to heat press the substrate 110 against the fabric of the garment 102, and a second bonding layer 170 composed of polyurethane film is coupled over the substrate 110 to further seal the substrate 110 between two bonding layers 160, 170 in relation to the garment 102. The second bonding layer 170 in the specific example includes cutouts corresponding to the signal conducting contacts 140, 145, such that the reference contact and biosensing contact surfaces are exposed through the second bonding layer 170, thus enabling contact between the contacts 140, 145 and the skin of a user. Thus, the first and the second bonding layers 160, 170 in the specific example encase the non-conductive region 150 and other components of the electrode system 100 (i.e., the substrate 110) while permitting the reference contact 145 and the set of biosensing contacts 140 to be exposed through the second bonding layer 170 and to interface with the skin of a user.

The system 100 can include any other suitable elements configured to enhance coupling of electrode elements to a body region of a user, to dissipate static, to enable removal of common-mode noise from the body of a user, to prevent moisture damage to elements of the system 100, and/or to facilitate manufacturing of the system 100. Furthermore, as a person skilled in the art will recognize from the previous detailed description and from the figures, modifications and changes can be made to the electrode system 100 without departing from the scope of the electrode system 100.

2. Method of Manufacture

Figure 10:
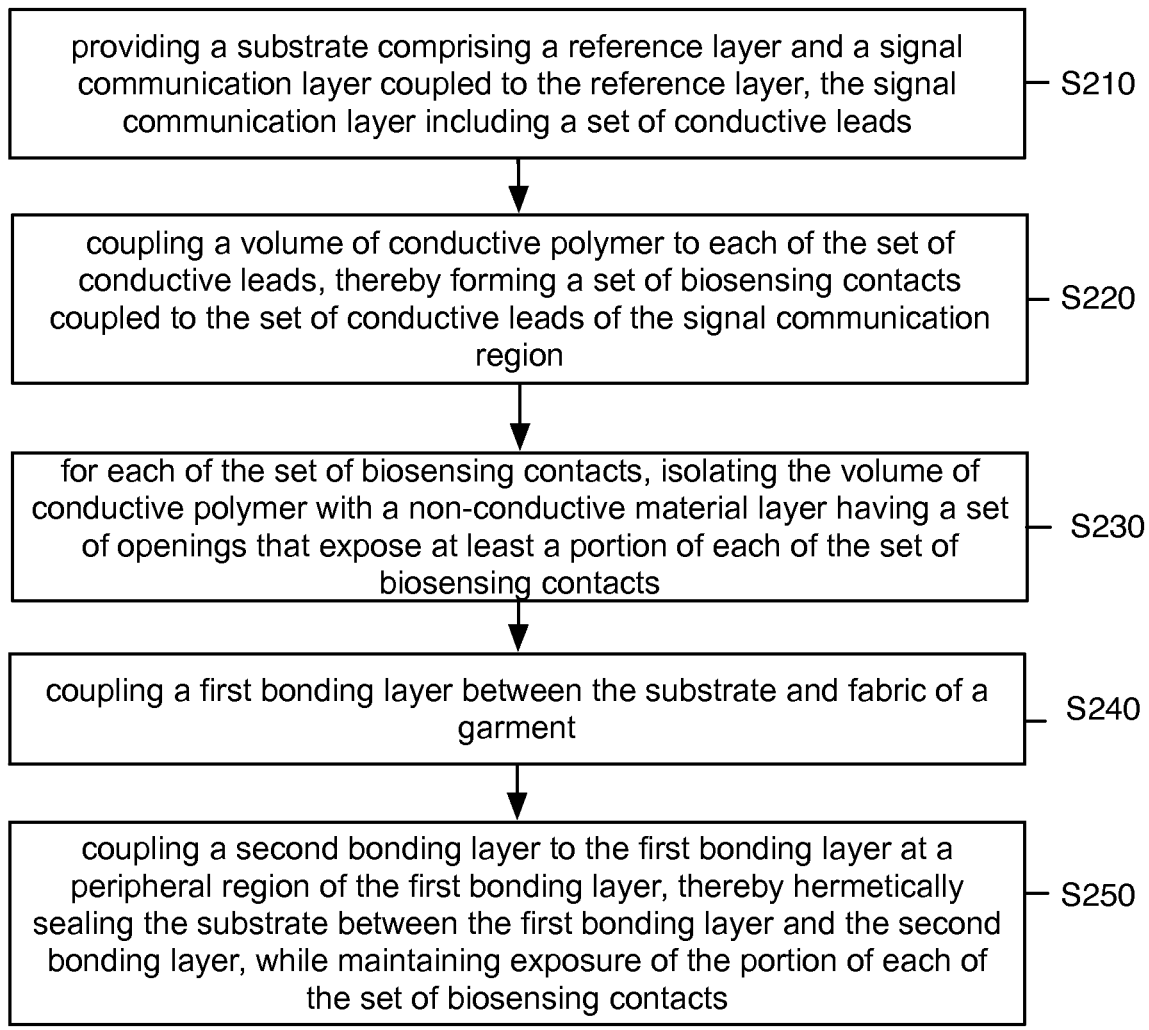
FIG. 10 depicts an embodiment of a method for manufacturing an electrode system.

As shown in FIG. 10, an embodiment of a method 200 for manufacturing an electrode system comprises: providing a substrate comprising a reference layer and a signal communication layer coupled (e.g., mechanically coupled, electrically coupled) to the reference layer, the signal communication layer including a set of conductive leads S210; coupling a volume of conductive polymer to each of the set of conductive leads, thereby forming a set of biosensing contacts coupled to the set of conductive leads of the signal communication region S220; for each of the set of biosensing contacts, isolating the volume of conductive polymer with a non-conductive material layer having a set of openings that expose at least a portion of each of the set of biosensing contacts S230; coupling a first bonding layer between the substrate and fabric of a garment S240; and coupling a second bonding layer to the first bonding layer at a peripheral region of the first bonding layer, thereby sealing the substrate between the first bonding layer and the second bonding layer, while maintaining exposure of the portion of each of the set of biosensing contacts S250.

The method 200 functions to produce an electrode system that is coupleable to a garment intended to be worn by a user while the user performs a physical activity. In particular, the method 200 functions to produce an electrode system that is resistant to damage by fluid associated with an activity performed by an individual, and that maintains contact with the user as the user performs the activity. As such, the method 200 can provide an electrode system configured to detect one or more of: electromyograph (EMG) signals, electrocardiography (ECG) signals, electroencephalograph (EEG) signals, galvanic skin response (GSR) signals, bio-electric impedance (BIA) and any other suitable biopotential signal of the user. The method 200 is preferably implemented at least in part at an embodiment of the system 100 described in Section 6 above; however, the method 200 can alternatively be implemented at any other suitable system for detection and processing of biometric signals from a user who is performing a physical activity.

In some embodiments, the method 200 can produce an embodiment, variation, or example of the electrode system 100 described in Section 6 above; however, in other embodiments, sub-portions of the method 200 can be adapted to manufacturing portions of any other suitable electrode system Furthermore, Blocks of the method 200 (e.g., blocks related to forming and coupling of elements) can be performed in any suitable order, variations of which are described below.

Block S210 recites: providing a substrate comprising a reference layer and a signal communication layer coupled (e.g., mechanically coupled, electrically coupled) to the reference layer, the signal communication layer including a set of conductive leads, which functions to provide a first portion of the electrode system that provides coupling regions for a set of biosensing contacts. In embodiments, variations, and examples, the substrate is preferably the substrate described in Section 6.2.1 above, which in some variations can omit the reference layer; however, in other variations, the substrate can comprise any other suitable substrate having conductive leads intended to interface with a set of biosensing contacts.

Block S220 recites: coupling a volume of conductive polymer to each of the set of conductive leads, thereby forming a set of biosensing contacts coupled to the set of conductive leads of the signal communication region of the substrate. In relation to the conductive polymer, Block S220 can further include forming at least one reference contact configured to couple to the reference region of the substrate, in variations wherein the electrode system includes a reference contact. Preferably, the volume of conductive polymer comprises a conductive silicone material that is compliant to some degree, impermeable to fluid, electrically conductive, and readily bondable to other elements of the electrode system; however, the volume of conductive polymer can alternatively comprise any other suitable material (e.g., polymeric material, composite material, conductive material, etc.). In one variation, Block S220 can comprise injection molding volumes of the conductive polymer in a flow state onto the signal communication region of the substrate, proximal the set of conductive leads, and transitioning the conductive polymer to a set state that maintains the morphological configurations of the set of biosensing contacts. In a second variation, Block S220 can comprise printing (e.g., with a stencil) volumes of the conductive polymer in a flow state onto the signal communication region of the substrate, proximal the set of conductive leads, and transitioning the conductive polymer to a set state that maintains the morphological configurations of the set of biosensing contacts. In still other variations, Block S220 can include one or more of: screen printing processes, stenciling processes, ink-jet printing processes to couple the set of biosensing contacts to the set of conductive leads of the substrate. In any of these variations, as noted in Section 1 above, Block S110 can include providing a substrate with one or more of: a set of openings, a set of recesses, an abraded surface, and an adhesive primer, to enhance coupling of the conductive polymer to the desired region(s) of the substrate in Block S220. Alternatively, Block S220 can include coupling a cured piece of the conductive polymer to at least one of the set of conductive leads, for instance, using a conductive adhesive material for coupling. For instance, volumes of the conductive polymer can be printed or otherwise applied onto transfer paper to form a set of conductive geometries (e.g., set conductive polymer), after which the conductive geometries are positioned at suitable locations of the substrate and coupled to the substrate (e.g., using a thermal bonding process). Finally, the transfer paper can be removed. In variations of this method, the transfer paper surface can have a texture that provides a surface texture at each of the set of contacts.

In relation to elements associated with the set of biosensing contacts described in Section 6.2.2 above, and as shown in FIG. 11, Block S220 can further include forming a surface feature comprising a set of protrusions at a surface of at least one of the set of biosensing contacts configured to face skin of the user, wherein the set of protrusions facilitates maintenance of contact between the electrode system and skin of the user S221. In Block S221, the set of protrusions can be formed using one or more of: a molding process, a casting process, a printing process, and any other suitable process. Block S220 can, however, include any other steps associated with formation of features described in Section 6.2.2 above.

Furthermore, as noted above, variations of the method 200 can comprise coupling the volumes of the conductive polymer to the set of conductive leads prior to and/or after coupling of the non-conductive region to a fabric patch or fabric of the garment in Block S230, which is described further in Section 2.1 below.

Block S230 recites: for each of the set of biosensing contacts, isolating the volume of conductive polymer with a non-conductive material layer having a set of openings that expose at least a portion of each of the set of biosensing contacts. Block S230 functions to form a barrier between each contact of the electrode system, in order to prevent bridging of contacts in an undesired manner. In one variation, Block S230 can comprise coupling the non-conductive material of the material layer directly to a fabric patch, wherein the fabric patch is backed with a bonding layer configured to interface with a first bonding layer coupled to a backside of the substrate. As such, the first bonding layer can couple the substrate to a garment, and the bonding layer coupled to the fabric patch can seal the substrate between two bonding layers, as described above. As such, the first bonding layer can couple the substrate to a garment and a second bonding layer in a manner that encapsulates the substrate, while enabling coupling of the second bonding layer to a fabric layer (e.g., for user comfort). In particular, a set of openings in the second bonding layer, as described above, is configured to provide access to the signal conducting region of the substrate for coupling of the set of biosensing contacts to the set of conductive leads of the signal conducting region. Thus, upon coupling of the set of biosensing contacts to the set of conductive leads, the substrate 110 is entirely sealed (e.g., from liquid penetration).

In this variation, Block S230 can comprise coupling (e.g., heat pressing, using an adhesive, using a chemical bond, etc.) the non-conductive material layer to a fabric patch which is backed with a bonding layer (e.g., polyurethane film), and cutting openings through the non-conductive material layer, the fabric patch, and the bonding layer in a configuration that corresponds to the set of biosensing contacts of Block S220. As such, the conductive polymer of the contacts of Block S220 can be applied within the openings of the non-conductive region, to ultimately couple to the set of conductive leads of the substrate.

Alternatively, Block S230 can comprise coupling the non-conductive material layer directly to the substrate (e.g., using an adhesive primer, etc.) or any other suitable portion of the electrode system, that allows sensitive portions of the substrate to be sealed between bonding layers. In one variation, the conductive polymer material of Block S220 can be coupled to the set of conductive leads of the substrate in a controlled manner, and the non-conductive material layer can be coupled (e.g., over-molded, applied in a cured state, etc.) to regions of the substrate around each of the volumes of conductive polymer, to isolate each of the set of contacts. Variations of Block S230 can, however, be implemented in any other suitable manner.

In Block S230, the non-conductive material layer is preferably composed of a material that readily couples with the polymer material of the set of biosensing contacts of Block S220. In one variation, the non-conductive material layer is composed of a non-conductive silicone material. However, in alternative variations, the non-conductive material layer can alternatively be composed of any other suitable material having low conductivity (e.g., insulating properties), that is otherwise configured to couple to the conductive polymer of Block S220 in any other suitable manner.

In as indicated above, Block S230 can comprise over-molding a volume of the non-conductive material layer in a flow state onto at least one of the fabric patch and the substrate, and transitioning the non-conductive material to a set state. In a second variation, Block S230 can comprise printing (e.g., 3D printing) the non-conductive material layer in a flow state onto at least one of the fabric patch and the substrate, and transitioning the non-conductive material to a set state. In still other variations, Block S230 can include one or more of: screen printing processes, stenciling processes, ink-jet printing processes, and any other suitable processes to couple the non-conductive material to at least one of the fabric patch and the substrate. In any of these variations, as noted in Section 1 above, Block S110 can include providing a substrate with one or more of: a set of openings, a set of recesses, an abraded surface, and an adhesive primer, to enhance coupling of the non-conductive material to the desired region(s) of the substrate in Block S230. Alternatively, Block S230 can include coupling a cured piece of the non-conductive material layer to at least one of the fabric patch and the substrate (e.g., with an adhesive).

As shown in FIG. 12, and in relation to elements associated with the non-conductive region described in Section 6.2.3 above, Block S230 can further include: forming a surface feature comprising a set of protrusions at a surface of the non-conductive material layer configured to face skin of the user, wherein the set of protrusions facilitates maintenance of contact between the electrode system and skin of the user S231. In Block S231, the set of protrusions can be formed using one or more of: a molding process, a casting process, a printing process, and any other suitable process. Additionally or alternatively, Block S230 can include: applying a barrier of a porous material (e.g., porous foam) configured at the non-conductive material layer, between each of the set of biosensing contacts, wherein the barrier prevents sweat or other moisture from bridging contacts of the set of biosensing contacts S232. In Block S232, the barrier can be formed using one or more of: a molding process, a casting process, a printing process, an adhesive application process, and any other suitable process. Block S230 can, however, include any other steps associated with formation of features described in Section 6.2.3 above.

Furthermore, as noted above, variations of the method 200 can comprise coupling of the non-conductive region to a fabric patch or fabric of the garment in Block S230, after which volumes of the conductive polymer, associated with Block S220, are applied within a set of openings of the non-conductive region, which is described further in Section 2.1 below. As such, Blocks S220 and S230 can be performed in any suitable order.

Block S240 recites: coupling a first bonding layer between the substrate and fabric of a garment, which functions to couple the substrate to fabric of the garment. Block S240 further functions to form a first portion of a bonding region that seals sensitive portions of the substrate and protects the substrate from moisture. In Block S240, the first bonding layer is preferably composed of a hydrophobic material that is impermeable to fluids; however, the material of the first bonding layer used in Block S240 can alternatively be non-hydrophobic while still being impermeable to fluids. In one variation, Block S240 comprises thermally bonding polyurethane film between the substrate and fabric of the garment, wherein the polyurethane film can be thermally bonded to the second bonding layer of Block S250 and/or other elements of the system; however, variations of Block S240 can comprise coupling a first bonding layer composed of any other suitable material (e.g., polymeric material) that is bondable to other elements of the system in any other suitable manner (e.g., by adhesive bonding, etc.). Furthermore, in order to enhance the strength of bonding between the first bonding layer of Block S240 and the second bonding layer of Block S250, the first and the second bonding layers are preferably composed of identical materials; however, in alternative variations, the first and the second bonding layers can alternatively be composed of different materials.

In relation to other blocks of the method 200, Block S240 can be performed simultaneously with one or more of: Blocks S210, S220, S230, and S250, for instance, in relation to coupling processes involving thermal bonding. Alternatively, Block S240 can be performed prior to or after any of the blocks of the method 200, as appropriate for any other suitable method of coupling the first bonding layer between the substrate and fabric of the garment.

Block S250 recites: coupling a second bonding layer to the first bonding layer at a peripheral region of the first bonding layer, thereby sealing the substrate between the first bonding layer and the second bonding layer, while maintaining exposure of the portion of each of the set of biosensing contacts. Block S250 functions to form a second portion of a bonding region that seals sensitive portions of the substrate and protects the substrate from moisture. In Block S250, the second bonding layer is preferably composed of a hydrophobic material that is impermeable to fluids; however, the material of the second bonding layer used in Block S250 can alternatively be non-hydrophobic while still being impermeable to fluids. Furthermore, in order to enhance the strength of bonding between the first bonding layer of Block S240 and the second bonding layer of Block S250, the first and the second bonding layers are preferably composed of identical materials; however, in alternative variations, the first and the second bonding layers can alternatively be composed of different materials.

In one variation, Block S250 comprises thermally bonding polyurethane film to a first broad surface of a fabric patch, wherein the non-conductive material layer is coupled to a second broad surface of the fabric patch. In this variation, Block S250 further comprises cutting a set of openings (i.e., corresponding to the set of biosensing contacts) through the non-conductive material layer, the fabric patch, and the second bonding layer, and coupling the second bonding layer to the first bonding layer using a thermal bonding process, thereby sealing the substrate between the bonding layers. In this variation, the assembly comprising non-conductive material layer, the fabric patch, and the second bonding layer can be applied over the substrate, with the set of conductive leads exposed through the openings, and the conductive polymer material can be coupled within the set of openings to the set of conductive leads in Block S220. As such, the second bonding layer can be coupled to the first bonding layer at a peripheral region of the first bonding layer, in a manner that seals at least a portion of the substrate between the bonding layers. However, variations of Block S250 can comprise coupling a second bonding layer composed of any other suitable material (e.g., polymeric material) to the first bonding layer and/or any other suitable elements of the system in any other suitable manner (e.g., by adhesive bonding, etc.). For instance, in relation to the variations described above and below, the second bonding layer can comprise or otherwise be coupled a fabric layer configured to interface with skin of the user, thereby enhancing comfort of the system 100 while the system 100 interfaces with the body of the user. In particular, the fabric layer-second bonding layer assembly can include a set of openings, as described in relation to the system 100 above and variations of manufacture below, wherein the set of openings provide access to a set of conductive leads for coupling to a set of biosensing contacts.

Variations of manufacture are described in Section 2.1 below.

2.1 Method of Manufacture—Variations

Figure 13:
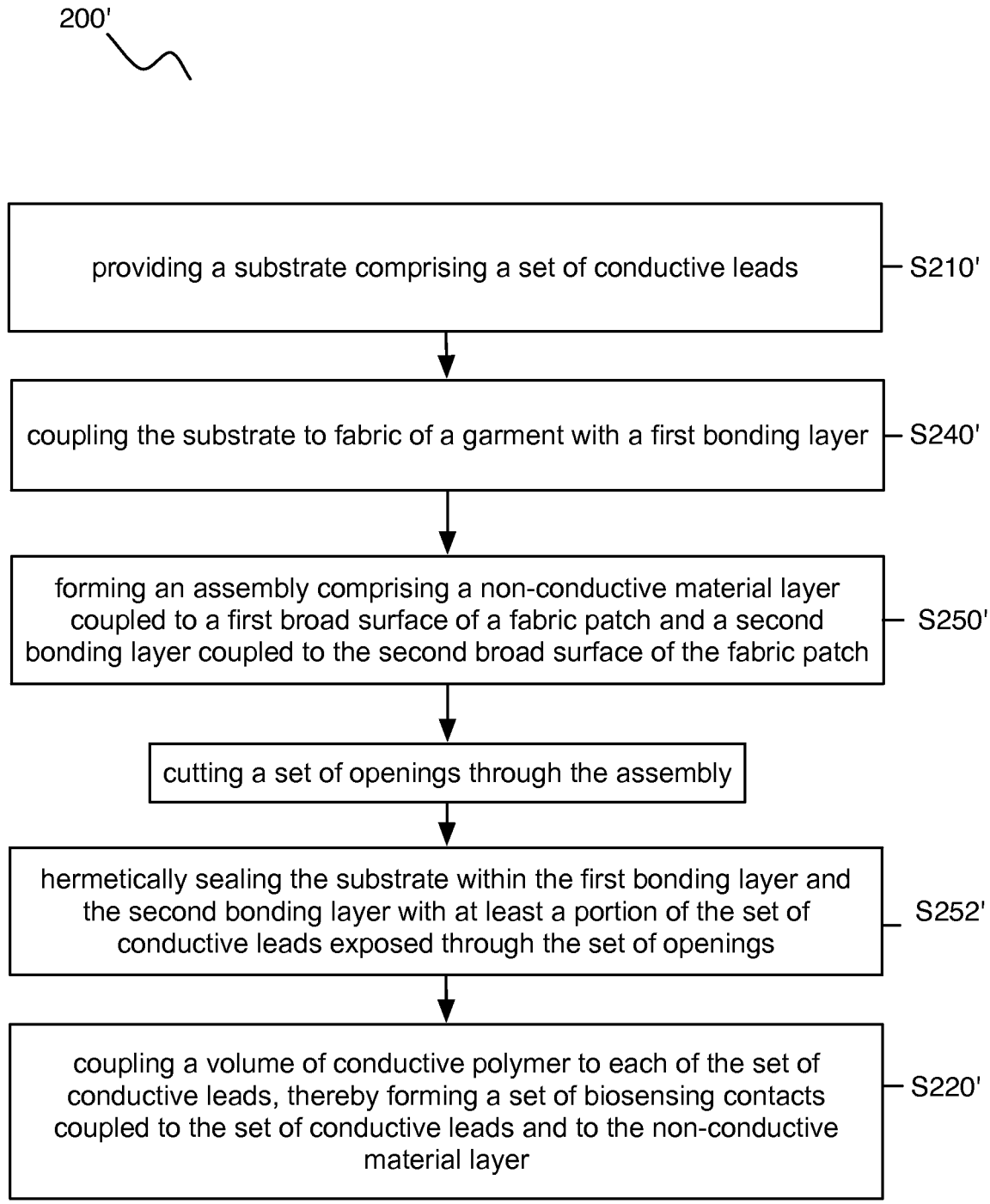
FIG. 13 depicts a variation of a method for manufacturing an electrode system.

In a first variation, as shown in FIG. 13, the method 200' can include: providing a substrate comprising a set of conductive leads S210'; coupling the substrate to fabric of a garment with a first bonding layer S240'; forming an assembly comprising a non-conductive material layer coupled to a first broad surface of a fabric patch and a second bonding layer coupled to the second broad surface of the fabric patch S250', wherein Block S250' includes cutting a set of openings through the assembly; sealing the substrate within the first bonding layer and the second bonding layer S252', with at least a portion of the set of conductive leads exposed through the set of openings; and coupling a volume of conductive polymer to each of the set of conductive leads, thereby forming a set of biosensing contacts coupled to the set of conductive leads and to the non-conductive material layer S220'.

In one specific application of this method 200', as shown in FIG. 14A, a substrate comprising a set of conductive copper leads can be coupled to fabric of a garment with a first bonding layer. Then, an assembly comprising a polyurethane-backed fabric patch (i.e., a fabric patch with a second bonding layer), coupled to a non-conductive silicone layer and having a set of openings through the assembly can be coupled to the first bonding layer, thereby sealing the substrate, while leaving the set of conductive copper leads exposed through the set of openings of the assembly. Finally, conductive silicone material can be stenciled into the set of openings, thereby coupling the conductive polymer to the set of conductive leads and to the non-conductive silicone layer, to form the set of biosensing contacts.

In another specific application of this method 200', as shown in FIG. 14B, a substrate comprising a set of conductive copper leads can be coupled to fabric of a garment with a first bonding layer. Then, an assembly comprising a polyurethane-backed fabric patch (i.e., a fabric patch with a second bonding layer), coupled to a non-conductive silicone layer and having a set of openings through the assembly can be formed, wherein the non-conductive silicone layer is abraded (e.g., with sand paper) and wiped clean to remove debris (e.g., with alcohol). In this specific application, the assembly is then coupled to the first bonding layer, thereby sealing the substrate, while leaving the set of conductive copper leads exposed through the set of openings of the assembly. Next, a primer can be applied to the abraded non-conductive silicone layer and edges of the set of openings. Finally, conductive silicone material can be stenciled into the set of openings and pressed with heat, thereby coupling the conductive polymer to the set of conductive leads and to the non-conductive silicone layer, to form the set of biosensing contacts.

In yet another specific application of this method 200', as shown in FIG. 14C, a substrate comprising a set of conductive copper leads can be coupled to fabric of a garment with a first bonding layer. Then, an assembly comprising a polyurethane-backed fabric patch (i.e., a fabric patch with a second bonding layer) and having a set of openings through the assembly can be formed. In this specific application, the assembly is then coupled to the first bonding layer, thereby sealing the substrate, while leaving the set of conductive copper leads exposed through the set of openings of the assembly. Next, a primer can be applied to the edges of the set of openings. Finally, conductive silicone material can be stenciled into the set of openings and pressed with heat, thereby coupling the conductive polymer to the set of conductive leads and to the non-conductive silicone layer, to form the set of biosensing contacts.

Figure 15:
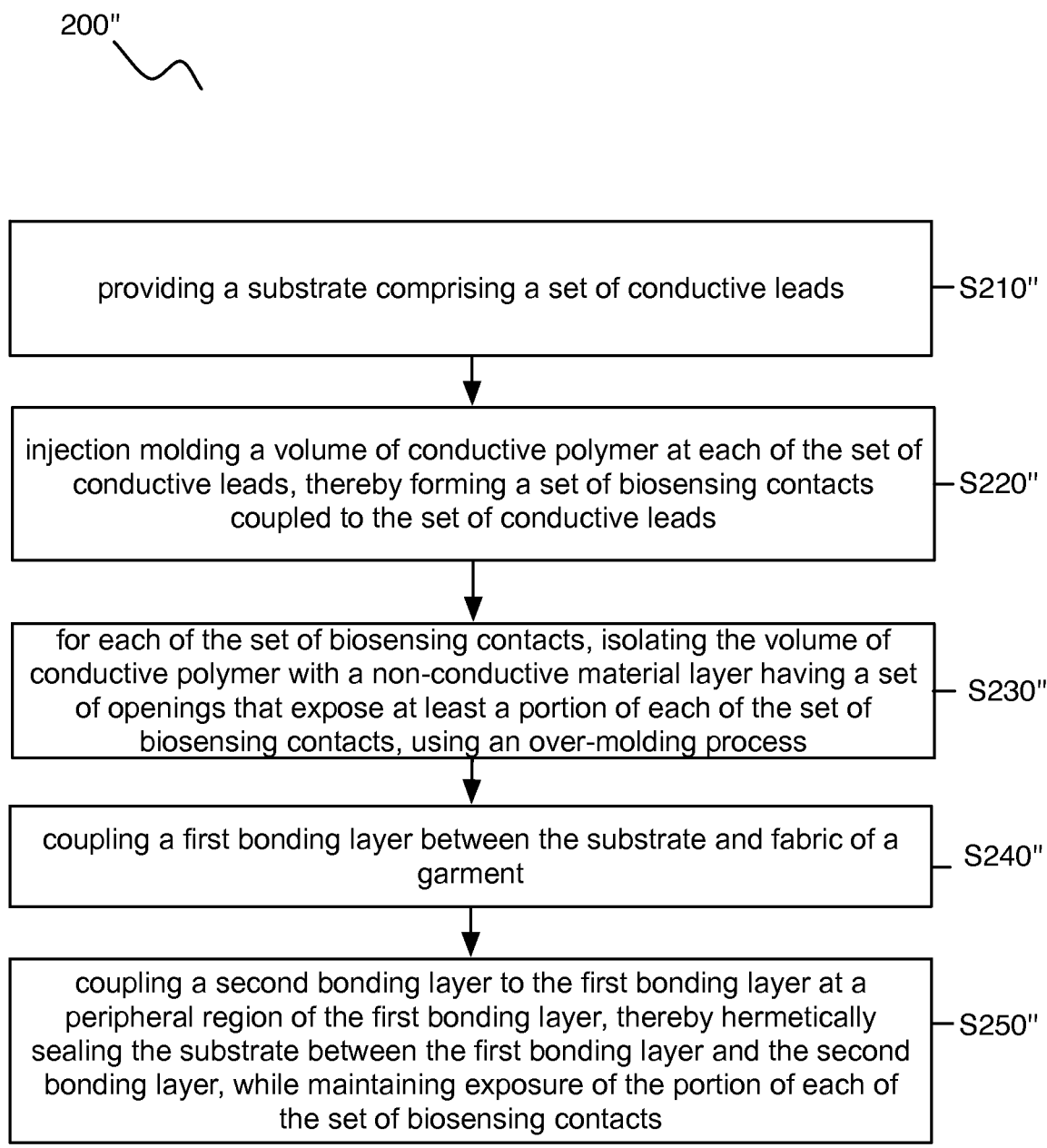
FIG. 15 depicts an alternative variation of a method for manufacturing an electrode system.

As shown in FIG. 15, an alternative variation of the method 200" can comprise: providing a substrate comprising a set of conductive leads S210"; injection molding a volume of conductive polymer at each of the set of conductive leads, thereby forming a set of biosensing contacts coupled to the set of conductive leads S220"; for each of the set of biosensing contacts, isolating the volume of conductive polymer with a non-conductive material layer having a set of openings that expose at least a portion of each of the set of biosensing contacts, using an over-molding process S230"; coupling a first bonding layer between the substrate and fabric of a garment S240"; and coupling a second bonding layer to the first bonding layer at a peripheral region of the first bonding layer, thereby sealing the substrate between the first bonding layer and the second bonding layer, while maintaining exposure of the portion of each of the set of biosensing contacts S250". This variation of the method 200" can include simultaneously molding the non-conductive material layer with fabric of the garment, in cooperation with coupling of the first bonding layer and the second bonding layer, thereby simultaneously coupling elements of the electrode system together.

In yet another alternative variation of the method, a non-conductive region can be formed, for subsequent coupling to material of the set of biosensing contacts. In this variation, the non-conductive region can comprise one or more of: a fabric material, a non-conductive material (e.g., polymer material), and any other suitable material that couples to the material of the set of biosensing contacts. In a specific example, the non-conductive region comprises a fabric layer with a coating of non-conductive silicone coupled to the fabric layer, wherein the non-conductive region is configured to provide a high friction (e.g., non-slip) surface upon interfacing with skin of the user. Thus, the non-conductive region can maintain positioning of the set of biosensing contacts at the skin of the user, and prevent noise from being generated due to motion of the system 100 relative to skin of the user.

In this alternative variation, a set of openings can be formed in the non-conductive region, wherein the set of openings corresponds to a desired configuration of the set of biosensing contacts, in correspondence with the set of conductive leads, to which the set of biosensing contacts is coupled. In this variation, forming the set of openings can comprise a cutting method (e.g., laser cutting, punching, etc.); however any other suitable method of forming openings can be used. Furthermore, variations of the alternative method can involve mass production of non-conductive regions for multiple electrode systems, wherein the non-conductive regions can be separated from each other at subsequent processing stages, thereby increasing efficiency in handling during manufacture of the electrode system.

In this alternative variation, the non-conductive region can then be positioned (e.g., with positioning/alignment features) into an injection molding apparatus, after which conductive polymer material (e.g., conductive silicone, conductive elastomer, etc.) of the set of biosensing contacts is injected into the set of openings of the non-conductive region. The conductive polymer material can then be cured (e.g., by heating, etc.) to increase durability. In this portion of the alternative variation of the method 200, one or more primers can be used to coupling the conductive polymer material to the non-conductive material. Additionally or alternatively, any other suitable method of depositing the conductive polymer material (e.g., compression molding, screen printing, mask printing, etc.) can be used. Furthermore, in this alternative variation, a recessed region at a "backside" of each of the set of biosensing contacts can be formed (e.g., based upon a feature of the mold used in the molding process), in order to facilitate subsequent bonding of the set of biosensing contacts to the set of conductive leads.

In this alternative variation, to facilitate coupling of the non-conductive region/set of biosensing contacts over the set of conductive leads, a first bonding layer, having a set of openings corresponding to the set of biosensing contacts can be coupled to the non-conductive region (e.g., based upon a thermal bonding process, based upon a spraying-application process, based upon any other suitable process). Finally, a conductive adhesive material can be applied to each of the set of biosensing contacts, for coupling of the set of biosensing contacts to the set of conductive leads. In a specific example, a volume of uncured conductive silicone can be applied into a recess at the "backside" of each biosensing contact, and/or to each conductive lead, and the set of biosensing contacts can thus be coupled to the set of conductive leads (e.g., using a thermal bonding process, using pressure, etc.)

Embodiments, variations, and examples of the method 200 can thus generate an electrode system that is thinner, lighter, and resource efficient, using a process that is less labor-intensive.

Variations of the system 100 and method 200 include any combination or permutation of the described components and processes. Furthermore, various processes of the preferred method can be embodied and/or implemented at least in part as a machine configured to receive a computer-readable medium storing computer-readable instructions. The instructions are preferably executed by computer-executable components preferably integrated with a system and one or more portions of the control module 155 and/or a processor. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A system comprising:
   a substrate defining a broad surface and comprising a signal communication region;
   a set of conductive leads supported by the broad surface of the substrate and electrically coupled to the signal communication region;
   a set of one or more biosensing contacts coupled to the set of conductive leads, each biosensing contact of the set of biosensing contacts composed of a conductive polymer;
   a non-conductive material comprising, for each biosensing contact, an opening such that a portion of the biosensing contact is exposed through the opening and protrudes through the opening, the system further comprising a body of porous material coupled to the non-conductive material adjacent to a biosensing contact of the set of one or more biosensing contacts and configured to prevent bridging of the set of one or more biosensing contacts by fluid diversion;
   a first bonding layer coupled to a garment; and
   a second bonding layer coupled to the first bonding layer such that the substrate, with the set of conductive leads, is retained and sealed between the first bonding layer and the second bonding layer,
   wherein the system is coupled to the garment, the system configured to sense biometric signals of a user wearing the garment.

2. The system of claim 1, wherein the first or second bonding layer includes, for each conductive lead, a corresponding opening and wherein each conductive lead is coupled to a biosensing contact via the corresponding opening.

3. The system of claim 1, wherein each exposed portion of a biosensing contact abuts skin of a user when the user is wearing the garment, and wherein the non-conductive material includes a surface component that increases friction between the non-conductive material and the skin of the user.

4. The system of claim 3, wherein the surface component comprises a set of protrusions arranged around one or more of the biosensing contacts.

5. The system of claim 1, further comprising a reference shield separating the set of biosensing contacts from the garment and coupled to a reference region defined at the broad surface of the substrate.

6. The system of claim 5, further comprising a reference contact exposed through and protruding through a reference contact opening of the non-conductive material, the reference contact positioned between the set of biosensing contacts and coupled to the reference region of the substrate.

7. The system of claim 1, wherein one or both of the first bonding layer and the second bonding layer create a water-tight seal between the substrate and a user when the user is wearing the garment.

8. The system of claim 1, further comprising a controller coupled to the set of conductive leads and configured to receive signals from the biosensing contacts via the conductive leads.

9. The system of claim 1, wherein the second bonding layer is coupled to the first bonding layer with a patch coupled between the second bonding layer and the first bonding layer, wherein the patch includes, for each conductive lead, an opening enabling the conductive lead to couple to a corresponding biosensing contact via the opening.

10. A system comprising:
    a substrate defining a broad surface and comprising a signal communication region;
    a set of one or more conductive leads supported by the broad surface of the substrate and electrically coupled to the signal communication region, wherein the substrate and the set of one or more conductive leads is retained and sealed between a first bonding layer and a second bonding layer;
    a set of one or more biosensing contacts coupled to the set of conductive leads; and
    a non-conductive material covering the set of biosensing contacts such that each biosensing contact is electrically isolated from every other biosensing contact, the non-conductive material comprising, for each biosensing contact, an opening such that a portion of the biosensing contact protrudes through the opening, the non-conductive material comprising a barrier of porous material configured adjacent to a biosensing contact of the set of one or more biosensing contacts and configured to prevent bridging of the set of one or more biosensing contacts by fluid diversion.

11. The system of claim 10, wherein the first or second bonding layer includes, for each conductive lead, a corresponding opening and wherein each conductive lead is coupled to a biosensing contact via the corresponding opening.

12. The system of claim 10, further comprising a controller coupled to the set of conductive leads and configured to receive signals from the biosensing contacts via the conductive leads.

13. The system of claim 10, wherein the system is coupled to a garment, the garment configured to sense biometric signals of a user wearing the garment.

14. The system of claim 13, wherein each exposed portion of a biosensing contact abuts skin of the user, and wherein the non-conductive material further includes a surface component that increases friction between the non-conductive material and the skin of the user.

15. The system of claim 14, wherein the surface component comprises a set of protrusions arranged around one or more of the biosensing contacts.

16. The system of claim 13, wherein one or both of the first bonding layer and the second bonding layer create a water-tight seal between the substrate and skin of the user.

17. The system of claim 10, further comprising a reference shield separating the set of biosensing contacts from the garment and coupled to a reference region of the substrate.

18. The system of claim 17, further comprising a reference contact exposed through and protruding through a reference contact opening of the non-conductive material, the reference contact positioned between the set of biosensing contacts and coupled to the reference region of the substrate.

* * * * *